(12) United States Patent
Cheich et al.

(10) Patent No.: US 11,325,340 B2
(45) Date of Patent: May 10, 2022

(54) DUNNAGE CONVERSION MACHINE AND METHOD

(71) Applicant: Ranpak Corp., Concord Township, OH (US)

(72) Inventors: Robert C. Cheich, Independence, OH (US); David V. Murphy, Painesville, OH (US); Steven M. Toneff, Painesville, OH (US); Maurice Jozef Paulus Anthonius Savelberg, Partij (NL); Raymond Paulus Hubertus Nolle, Heerlen (NL); Pedro Erik Willem Winkens, Vaals (NL)

(73) Assignee: Ranpak Corp., Concord Township, OH (US)

( * ) Notice: Subject to any disclaimer, the term of this patent is extended or adjusted under 35 U.S.C. 154(b) by 158 days.

(21) Appl. No.: 15/604,982

(22) Filed: May 25, 2017

(65) Prior Publication Data

US 2017/0259522 A1    Sep. 14, 2017

Related U.S. Application Data

(60) Division of application No. 13/957,578, filed on Aug. 2, 2013, now Pat. No. 9,669,596, which is a division
(Continued)

(51) Int. Cl.
*B31D 5/00* (2017.01)
*B32B 3/28* (2006.01)
(Continued)

(52) U.S. Cl.
CPC .............. *B32B 3/28* (2013.01); *A63J 5/021* (2013.01); *B31D 5/0047* (2013.01);
(Continued)

(58) Field of Classification Search
CPC .. B31D 5/0047; B31D 5/0052; B31D 5/0039; B31D 2205/0047; B31D 2205/0058
(Continued)

(56) References Cited

U.S. PATENT DOCUMENTS 3,017,317 A    1/1962   Voigtman et al.
3,235,442 A *  2/1966   William ................ D01D 5/23
                                                    28/269
(Continued)

FOREIGN PATENT DOCUMENTS

CN        1147226      4/1997
CN        1152274      6/1997
(Continued)

*Primary Examiner* — Anna K Kinsaul
*Assistant Examiner* — Eyamindae C Jallow
(74) *Attorney, Agent, or Firm* — Renner, Otto, Boisselle & Sklar, LLP

(57) ABSTRACT

A dunnage conversion machine (36) converts a sheet stock material into a dunnage product that is relatively thicker and less dense than the stock material, but is relatively thin and sufficiently flexible to function as a protective wrap. The conversion machine includes a feed mechanism (40) that advances a sheet stock material therethrough and a connecting mechanism (42) downstream of the feed mechanism. The connecting mechanism retards the passage of the sheet stock material therethrough by feeding the stock material therethrough at a slower rate than the feed mechanism feeds the stock material to the connecting mechanism. This causes the stock material to randomly crumple in a longitudinal space between the feed mechanism and the connecting mechanism. The connecting mechanism connects multiple overlapping layers of sheet stock material together as they pass therethrough, including connecting at least one crumpled sheet to one side of one other sheet.

10 Claims, 36 Drawing Sheets

Related U.S. Application Data of application No. 13/470,444, filed on May 14, 2012, now abandoned, which is a continuation of application No. 13/094,165, filed on Apr. 26, 2011, now Pat. No. 8,177,697, which is a continuation of application No. 12/236,948, filed on Sep. 24, 2008, now Pat. No. 7,955,245.

(60) Provisional application No. 61/076,365, filed on Jun. 27, 2008, provisional application No. 61/035,701, filed on Mar. 11, 2008, provisional application No. 60/974,532, filed on Sep. 24, 2007.

(51) Int. Cl.
*A63J 5/02* (2006.01)
*B65D 81/03* (2006.01)

(52) U.S. Cl.
CPC ........... *B31D 5/0052* (2013.01); *B65D 81/03* (2013.01); *A63J 5/02* (2013.01); *B31D 2205/007* (2013.01); *B31D 2205/0035* (2013.01); *B31D 2205/0047* (2013.01); *B31D 2205/0058* (2013.01); *B31D 2205/0064* (2013.01); *B31D 2205/0082* (2013.01); *B31D 2205/0088* (2013.01); *Y10S 493/967* (2013.01); *Y10T 428/2495* (2015.01); *Y10T 428/24628* (2015.01); *Y10T 428/249922* (2015.04)

(58) Field of Classification Search
USPC ......... 493/350, 459, 464, 904, 967; 241/166
See application file for complete search history.

(56) References Cited

U.S. PATENT DOCUMENTS

| | | | | |
|---|---|---|---|---|
| 3,603,216 | A * | 9/1971 | Johnson | B31D 5/0047 493/359 |
| 3,799,039 | A * | 3/1974 | Johnson | B31D 5/0047 156/493 |
| 4,550,472 | A | 11/1985 | Temple et al. | |
| 4,557,716 | A | 12/1985 | Ottaviano | |
| 4,717,613 | A * | 1/1988 | Ottaviano | B31D 5/0047 156/493 |
| 4,750,896 | A * | 6/1988 | Komaransky | B31D 5/0047 493/357 |
| 4,950,218 | A * | 8/1990 | Tsuru | A01G 9/0295 493/346 |
| 5,131,903 | A | 7/1992 | Levine et al. | |
| 5,203,761 | A | 4/1993 | Reichental et al. | |
| 5,211,620 | A * | 5/1993 | Ratzel | B31D 5/0047 493/346 |
| 5,297,919 | A | 3/1994 | Reichental et al. | |
| 5,322,477 | A * | 6/1994 | Armington | B26D 1/30 493/346 |
| 5,387,173 | A * | 2/1995 | Simmons, Jr. | B31D 5/0047 493/407 |
| 5,439,730 | A | 8/1995 | Kelly | |
| 5,468,208 | A | 11/1995 | Armington et al. | |
| 5,558,923 | A * | 9/1996 | Vesamaa | B31D 5/006 428/137 |
| 5,571,067 | A | 11/1996 | Ratzel | |
| 5,593,376 | A | 1/1997 | Armington et al. | |
| 5,607,383 | A | 3/1997 | Armington et al. | |
| 5,637,071 | A | 6/1997 | Simmons et al. | |
| 5,643,167 | A * | 7/1997 | Simmons | B31D 5/0047 493/464 |
| 5,712,020 | A * | 1/1998 | Parker | B31D 5/006 428/152 |
| 5,836,538 | A | 11/1998 | Lencoski et al. | |
| 5,873,809 | A | 2/1999 | Kempster et al. | |
| 5,876,318 | A | 3/1999 | Ratzel | |
| 5,908,375 | A * | 6/1999 | Simmons | B31D 5/0047 493/346 |
| 5,924,971 | A | 7/1999 | Simmons | |
| 5,947,886 | A | 9/1999 | Simmons | |
| 6,017,299 | A | 1/2000 | Ratzel | |
| 6,019,715 | A | 2/2000 | Ratzel et al. | |
| 6,095,454 | A | 8/2000 | Simmons et al. | |
| 6,106,452 | A | 8/2000 | Baumuller | |
| 6,168,560 | B1 | 1/2001 | Pluymaekers et al. | |
| 6,176,818 | B1 * | 1/2001 | Simmons, Jr. | B31D 5/0047 493/346 |
| 6,210,310 | B1 * | 4/2001 | Manley | B31D 5/0047 493/464 |
| 6,387,029 | B1 | 5/2002 | Lencoski | |
| 6,676,589 | B2 | 1/2004 | Kung et al. | |
| 8,105,227 | B2 | 1/2012 | Hubbard et al. | |
| 8,435,165 | B2 * | 5/2013 | Bock | B31D 5/0047 493/405 |
| 2002/0119876 | A1 | 8/2002 | Lu et al. | |
| 2003/0139272 | A1 * | 7/2003 | Simmons, Jr. | B31D 5/0047 493/394 |
| 2004/0043883 | A1 | 3/2004 | Toth | |
| 2004/0142806 | A1 | 7/2004 | Coppus et al. | |
| 2005/0181924 | A1 | 8/2005 | Demers et al. | |
| 2005/0255982 | A1 | 11/2005 | Harding et al. | |
| 2007/0021286 | A1 | 1/2007 | Kobben | |
| 2007/0117705 | A1 | 5/2007 | Toth | |
| 2007/0123406 | A1 | 5/2007 | Demmers et al. | |
| 2007/0280847 | A1 | 12/2007 | Ratzel et al. | |
| 2007/0281847 | A1 | 12/2007 | Ratzel et al. | |
| 2008/0051277 | A1 | 2/2008 | Slovencik et al. | |
| 2008/0076654 | A1 | 3/2008 | Riga et al. | |
| 2008/0153685 | A1 * | 6/2008 | Cheich | B31D 5/0047 493/381 |
| 2009/0075800 | A1 | 3/2009 | Wetsch et al. | |
| 2009/0082187 | A1 * | 3/2009 | Cheich | B31D 5/0047 493/350 |
| 2010/0029456 | A1 | 2/2010 | Cheich | |
| 2010/0041534 | A1 | 2/2010 | Harding et al. | |
| 2010/0278577 | A1 | 11/2010 | Hubbard et al. | |
| 2011/0053750 | A1 | 3/2011 | Wetsch | |
| 2011/0230325 | A1 | 9/2011 | Harding et al. | |

FOREIGN PATENT DOCUMENTS

| | | |
|---|---|---|
| EP | 0 679 504 | 11/1995 |
| EP | 0650827 | 7/1997 |
| EP | 0573353 | 4/1998 |
| EP | 0 888 879 | 1/1999 |
| JP | 10505288 | 4/1995 |
| JP | 10500074 | 5/1995 |
| WO | 94/012344 | 6/1994 |
| WO | 94/27813 | 12/1994 |
| WO | 95/29055 | 11/1995 |
| WO | 95/31296 | 11/1995 |
| WO | 96/01731 | 1/1996 |
| WO | 01/89936 | 11/2001 |
| WO | 02/16120 | 2/2002 |
| WO | 2007/012753 | 2/2007 |

* cited by examiner

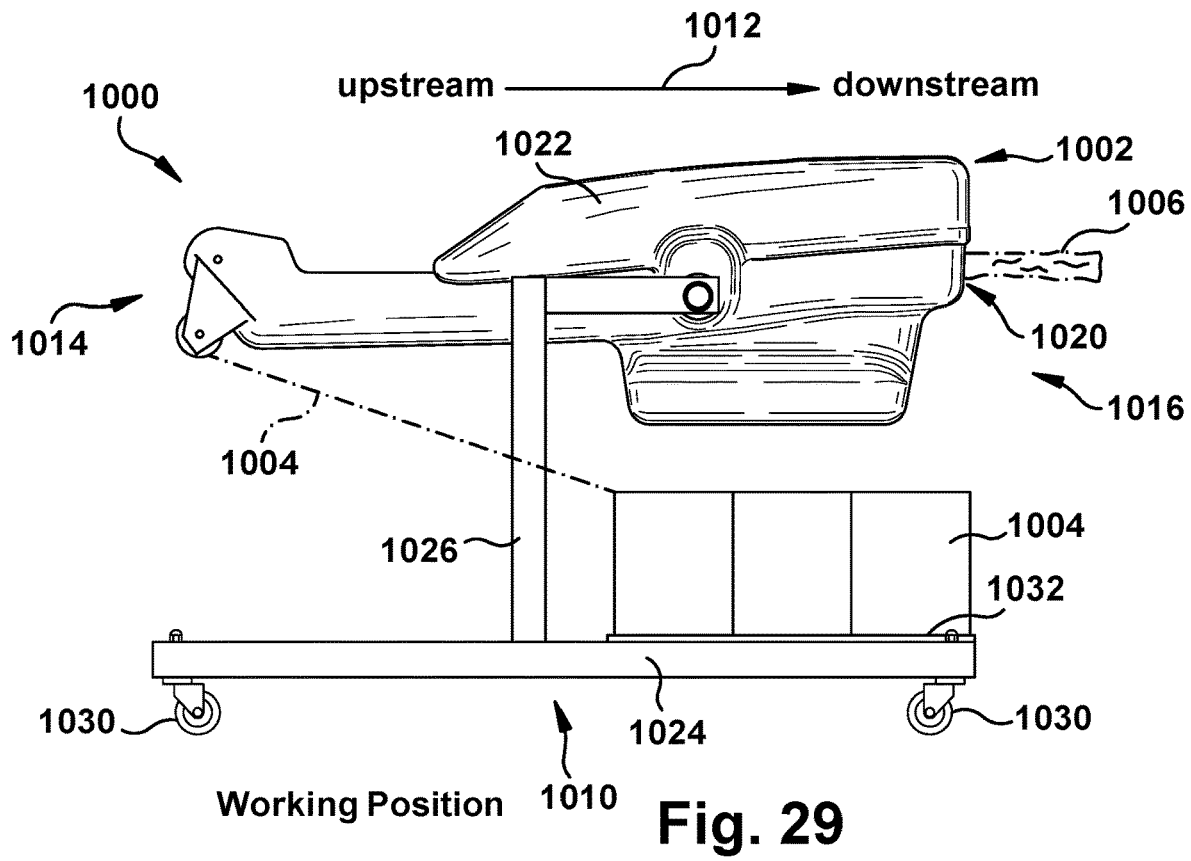
Fig. 29 Working Position
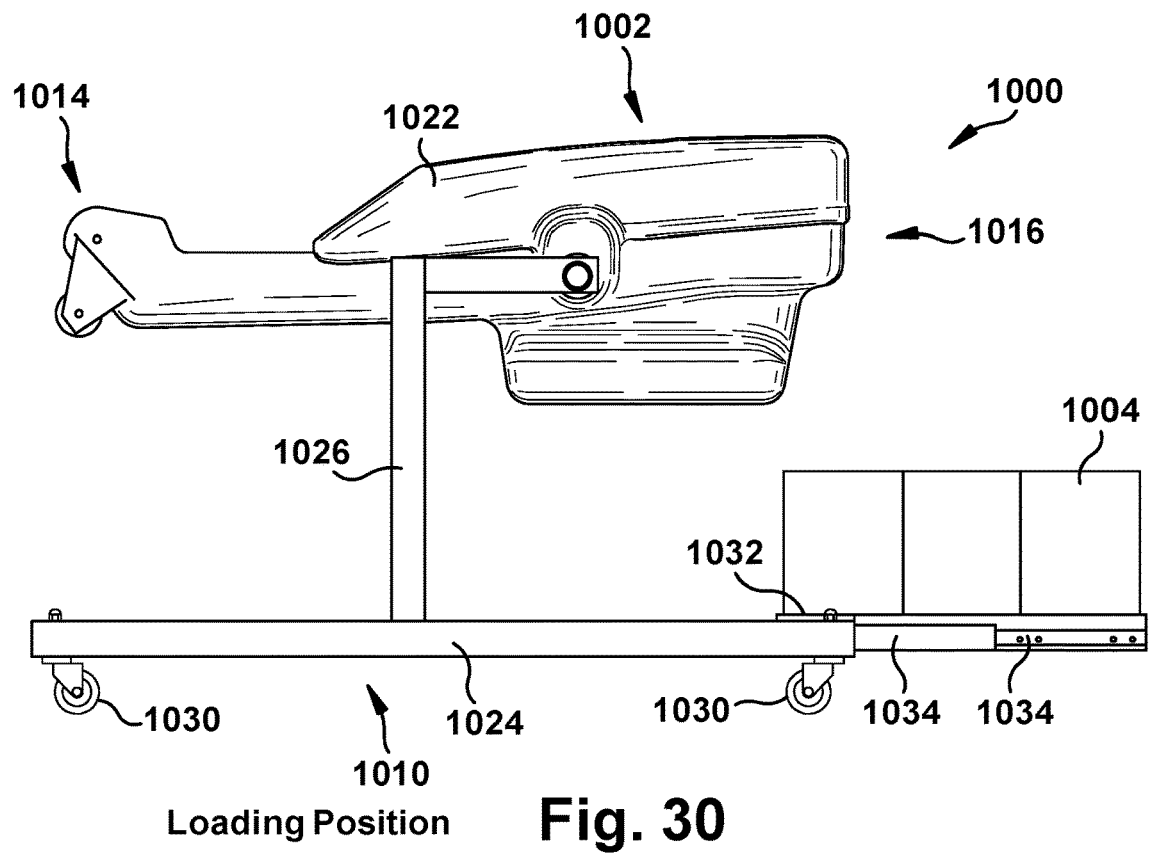
Fig. 30 Loading Position

DUNNAGE CONVERSION MACHINE AND METHOD

This application is a division of U.S. patent application Ser. No. 13/470,444, filed May 14, 2012; which is a divisional of U.S. patent application Ser. No. 13/094,165, filed Apr. 26, 2011, now U.S. Pat. No. 8,177,697; which is a continuation of U.S. patent application Ser. No. 12/236,948, filed Sep. 24, 2008, now U.S. Pat. No. 7,955,245; which claims the benefit of U.S. Provisional Patent Application Nos. 60/974,532, filed 24 Sep. 2007; 61/035,701, filed 11 Mar. 2008; and 61/076,365, filed 27 Jun. 2008, each of which is incorporated by reference.

FIELD OF THE INVENTION

The present invention is related to dunnage conversion machines, and more particularly to a stock supply assembly and an output chute for a dunnage conversion machine, and a corresponding method, as well as a dunnage conversion machine and method for making a wrappable dunnage product from a sheet stock material.

BACKGROUND

Dunnage conversion machines convert a stock material into a dunnage product that can be used to pack articles and thus minimize or prevent damage during shipment. The dunnage conversion machines, also referred to as dunnage converters, include a conversion assembly that converts a stock material into a relatively lower density dunnage product as the stock material moves through the conversion assembly from an upstream end toward an outlet at a downstream end.

At the upstream end of the converter, a supply of stock material is fed into the conversion assembly. The stock material typically is stored adjacent the conversion assembly, which consumes the stock material as it produces strips of dunnage from which dunnage products are severed. When the converter is deployed underneath a table or other work surface, keeping the stock material under the table keeps it out of the way, but makes replenishing the stock material difficult.

At the downstream end, dunnage conversion machines often include an output chute secured to the housing or frame of the converter to guide dunnage products away from the outlet. The output chute supports and guides the dunnage products and can prevent the exiting dunnage products from causing jams in the conversion assembly. A typical dunnage product has a length of about twenty to about seventy centimeters. If a dunnage product does not exit the output chute on its own, a subsequent dunnage product typically will push it out of the chute.

A wrappable dunnage product may be advantageous for layering, including placement between relatively flat items such as plates, and/or for individually wrapping articles such as fragile ornaments, glass lamps, or the wooden legs on fine furniture, to minimize or prevent damage during shipment. Not all dunnage is suitable for use as a wrapping product, however. Some dunnage products in pad form, for example, can be too narrow and/or stiff to be used effectively as a protective wrapping product.

Existing wrappable dunnage products include foldable cardboard and plastic bubble wrap. Unfortunately, both take up a lot space for storage until ready to use. Cardboard typically has a sinusoidal, regularly undulating ply glued to one or more generally planar plies. Some cardboard is made using pleating rollers that extend across the width of a sheet to form the regular sinusoidal shape as the sheet passes between the rollers. These pleating rollers are very expensive to make. Cardboard also is difficult to produce on demand since the glue holding the layers together has to dry before use. Therefore, on-demand conversion of a stock material into a cardboard-like wrapping dunnage product probably is not practical.

Unlike cardboard, plastic bubble wrap can be made on demand, but the process is very slow (generally about nine meters per minute, compared to about twenty meters per minute for some converters that produce paper dunnage) and its speed is limited by the nature in which bubble wrap is made. Additionally, plastic is increasingly expensive, as well as increasingly being seen as bad for the environment.

SUMMARY

We have developed a wrappable dunnage product that can be produced relatively quickly on demand from a sheet stock material for immediate use. An exemplary stock material is kraft paper, which is biodegradable, recyclable, and composed of a renewable resource.

More specifically, the present invention provides a wrappable dunnage product, a dunnage converter for converting a sheet stock material into a wrappable dunnage product, and a corresponding method for producing a wrappable dunnage product. In particular, the present invention provides a multiply dunnage product that has sufficient flexibility and loft to be used as a protective wrap. At least one layer of the dunnage product includes a randomly crumpled web or sheet. Randomly crumpling at least one sheet provides cushioning properties to the dunnage wrap, while lines of connection where the multiple overlaid sheets or plies are held together mechanically help the dunnage wrap retain its structure. These lines of connection also can provide convenient fold lines.

Additionally, a dunnage converter and method provided by the present invention can be employed to produce a wrappable dunnage product without employing pleating rollers. Although pleating rollers can be used to form regular folds in the stock material, they are relatively expensive and tend to provide different protective properties because the fold lines formed in the stock material are consistently parallel to each other.

An exemplary dunnage conversion machine for converting a sheet stock material into a wrapping dunnage product that is relatively thicker and less dense than the stock material includes a feed mechanism and a connecting mechanism downstream of the feed mechanism. The feed mechanism advances at least a first web of sheet stock material therethrough at a first rate. The connecting mechanism (a) retards the advancement of the sheet stock material by passing the sheet stock material therethrough at a second rate that is less than the first rate, thereby causing the first web to randomly crumple in a longitudinal space between the feed mechanism and the connecting mechanism, and (b) connects the crumpled first web to a second web to maintain the crumpled first web in its crumpled state. The second web may pass through the feed mechanism and crumple between the feed mechanism and the connecting mechanism, or bypass the feed mechanism and join the first web as an uncrumpled ply.

An exemplary dunnage product includes multiple plies of sheet stock material connected together, including at least one randomly crumpled sheet having an irregular pitch that is connected to one side of another sheet to maintain the crumpled sheet in its crumpled state. An exemplary stock material includes paper.

And an exemplary method for producing a dunnage product includes the following steps: (i) advancing at least a first web of sheet stock material through an upstream feed mechanism, (ii) retarding the passage of the sheet stock material downstream of the feed mechanism by passing the sheet stock material at a second rate that is less than the first rate to cause the first web to randomly crumple, and (iii) connecting multiple layers of sheet stock material, including connecting the crumpled first web to one side of a second web of sheet stock material, to hold the crumpled first web in its crumpled state.

Another dunnage conversion machine provided by the invention for converting a sheet stock material into a dunnage product includes a feed mechanism for advancing a sheet stock material therethrough at a first rate, and a connecting mechanism downstream of the feed mechanism that (a) retards the advancement of the sheet stock material by passing the sheet stock material therethrough at a second rate that is less than the first rate, thereby causing at least one sheet to randomly crumple in a longitudinal space between the feed mechanism and the connecting mechanism, and (b) mechanically connects multiple sheets of stock material together to hold the crumpled sheet in its crumpled state.

Yet another dunnage conversion machine for converting a sheet stock material into a dunnage product includes a feed assembly for advancing a sheet stock material therethrough at a first rate, and a connecting assembly downstream of the feed assembly that (a) advances the sheet stock material therethrough at a second rate that is less than the first rate, thereby causing at least one sheet of stock material to randomly crumple in a longitudinal space between the feed assembly and the connecting assembly, and b) mechanically connects multiple sheets together, including at least one crumpled sheet, to maintain the crumpled sheet in its crumpled state.

Another method for producing a dunnage product includes the steps of (i) advancing a sheet stock material at a first rate, and (ii) mechanically connecting multiple layers of sheet stock material together at a second rate that is less than the first rate to cause at least one sheet of stock material to randomly crumple within a confined space before being connected to another sheet to maintain the crumpled sheet in its crumpled state.

Still another dunnage conversion machine for converting a sheet stock material into a wrapping dunnage product includes (i) means for advancing a sheet stock material at a first rate, and (ii) means for mechanically connecting multiple layers of sheet stock material together at a second rate that is less than the first rate to cause at least one sheet of stock material to randomly crumple within a confined space before being connected to another sheet to maintain the at least one crumpled sheet in its crumpled state.

Other concepts provided by the present invention include: (i) means for guiding at least one sheet of stock material to a connecting means at the second rate so that at least one sheet that is connected to the crumpled sheet is not crumpled; (ii) a guide for guiding at least one sheet of stock material to the connecting mechanism and bypassing the feed mechanism to connect the crumpled sheet to an uncrumpled sheet to form a relatively flat wrapping dunnage product that retains its shape; (iii) a bunching assembly upstream of the feed mechanism that inwardly gathers the sheet stock material to encourage the formation of longitudinally-extending fold lines in the stock material; (iv) a separator that cooperates with channel guides to define multiple channels for the stock material to travel through the feed mechanism to the connecting mechanism, whereby the channels confine the stock material as it crumples between the feed mechanism and the connecting mechanism, and each channel has a different height to promote different frequencies and amplitudes in the crumpling of respective webs of sheet stock material, (v) laterally-spaced forming members that extend into the path of lateral edge portions of the sheet stock material to urge those lateral edge portions inward to reinforce the edges of the stock material as those edge portions pass through the connecting mechanism; (vi) a series of transversely-extending serpentine guides upstream of the feed mechanism that define a serpentine path for the sheet stock material to improve its tracking and maintaining a minimum tension in the stock material drawn therethrough; (vii) wherein the aforementioned serpentine guides include three parallel rollers arranged with the axes generally in a common plane, and at least one roller is pivotable between an operating position in line with the other rollers and a loading position spaced from the operating position to provide a large gap for threading the stock material therethrough; (viii) where the connecting mechanism includes at least one pair of gears that intermesh to connect the multiple layers of stock material, the gears include at least two laterally-spaced segments on opposing sides of an annular recess therebetween, and a stripper bar extends through the annular recess a distance upstream and downstream of the gears to help release the stock material from the gears; and (ix) wherein the feed mechanism includes at least one pair of rotating members that feed the stock material therebetween, and a mechanism for moving at least one of the rotating members away from the other to facilitate loading a sheet stock material therebetween.

We have found that relatively short dunnage products, having a length of less than about fifteen centimeters, for example, tend to shingle, twist, or otherwise jam and block passage through the output chute. And subsequent strips of dunnage add to the jam rather than pushing preceding dunnage products out of the chute.

By moving the output chute out of the way, relatively short dunnage products can take an alternate route or path and fall through a gravity chute rather than being fed into the output chute where they might jam.

An exemplary dunnage conversion machine provided by the present invention includes a conversion assembly for converting a stock material into a dunnage product and dispensing the dunnage product through an outlet. The conversion assembly is capable of producing dunnage products of multiple lengths. The conversion assembly also includes an output chute adjacent the outlet. The output chute is moveable between a first position where the output chute is aligned with the outlet so that dunnage products having at least a predetermined minimum length are dispensed through the outlet into the output chute, and a second position where the output chute is not aligned with the outlet so that dunnage products having a length less than the predetermined minimum length that are dispensed through the outlet bypass the output chute.

Another exemplary dunnage conversion machine provided by the invention includes a conversion assembly for converting a stock material into a dunnage product and for dispensing the dunnage product through an outlet. This conversion machine also includes an output chute adjacent the outlet. The output chute has walls that define a passage through the output chute. The output chute is moveable between a first position where the passage is aligned with the outlet to receive dunnage products, and a second position where the passage is not aligned with the outlet. The conversion machine also includes a controller that enables selection of a desired length of a dunnage product and controls the position of the outlet chute so that in its first position dunnage products dispensed through the outlet enter the passage through the output chute, and in its second position dunnage products dispensed through the outlet bypass the output chute.

Another exemplary dunnage conversion machine includes a conversion assembly for converting a stock material into a dunnage product as the stock material travels from an upstream end of the conversion assembly to a downstream end of the conversion assembly. The conversion assembly also includes a housing that defines an outlet for dispensing the dunnage product. The conversion machine also includes an output chute adjacent the outlet. The output chute has an upstream end that is moveable relative to the outlet between a first position where the upstream end of the output chute is aligned with the outlet to receive dunnage products from the conversion assembly, and a second position where the upstream end of the output chute is not aligned with the outlet so that dunnage products from the conversion assembly bypass the output chute.

Yet another dunnage conversion machine includes a conversion assembly for converting a stock material into a dunnage product as the stock material travels from an upstream end of the conversion assembly to a downstream end of the conversion assembly. The conversion assembly includes a housing that defines an outlet for dispensing the dunnage product. The conversion machine also includes a chute adjacent the outlet. The conversion assembly dispenses dunnage products through the outlet in a downstream direction. The chute has a gravity portion that extends in a direction transverse the downstream direction, and an output chute portion that is moveable between a first position where the upstream end of the output chute portion is aligned with the outlet and a second position where the upstream end of the output chute portion is spaced from the outlet. In the first position, the output chute portion closes the gravity portion, and in the second position the gravity chute portion is open to the outlet.

An exemplary method of dispensing dunnage products includes the steps of (a) converting a stock material into a dunnage product and dispensing the dunnage product through an outlet, (b) if the dunnage product has at least a predetermined minimum length, moving an upstream end of an output chute adjacent to and in alignment with the outlet to receive, support, and guide the dunnage product as it exists the outlet. If the dunnage product has a length that is less than the predetermined minimum length, the method includes the step of moving the upstream end of the output chute relative to the outlet so that dunnage products exiting the outlet bypass the output chute.

To make it easier to re-stock the supply of stock material, the present invention provides a shelf that slides out for restocking, away from the conversion assembly, and slides back in to be out of the way while the dunnage converter is operating.

An exemplary dunnage conversion machine provided by the present invention includes a shelf for supporting a supply of stock material, a conversion assembly for converting a stock material into a dunnage product, and a stand that supports the conversion assembly and the shelf. The shelf is linearly movable between an operating position adjacent the conversion assembly and a loading position spaced from the operating position for loading stock material without moving the conversion assembly.

The foregoing and other features of the invention are hereinafter fully described and particularly pointed out in the claims, the following description and annexed drawings setting forth in detail certain illustrative embodiments of the invention, these embodiments being indicative, however, of but a few of the various ways in which the principles of the invention may be employed.

BRIEF DESCRIPTION OF THE DRAWINGS

FIG. 29 is a side view of the dunnage conversion machine shown in FIG. 28 with the shelf in a working position.

FIG. 30 is a side view of the dunnage conversion machine shown in FIG. 28 with the shelf in a loading position.

DETAILED DESCRIPTION

The present invention provides a dunnage conversion machine and method for making a wrappable dunnage product from a sheet stock material, as well as a stock supply assembly and an output chute for a dunnage conversion machine, and corresponding methods.

Wrappable Dunnage

The present invention provides a wrappable dunnage product, a dunnage converter for converting a sheet stock material into a wrappable dunnage product, and a corresponding method for producing a wrappable dunnage product that is relatively thicker and less dense than the stock material. In particular, the present invention provides a multi-ply dunnage product that has sufficient flexibility and loft to be used as a protective layer or wrap. At least one ply of the dunnage product includes a randomly crumpled web or sheet. Randomly crumpling at least one sheet provides cushioning properties to the dunnage wrap. The crumpled sheet or sheets are held in the crumpled state along lines of mechanical interconnection with at least one other sheet, where the lines of connection where the multiple overlaid sheets or plies are held together can provide convenient fold lines.

Additionally, the dunnage converter and method provided by the present invention can be employed to produce a dunnage product relatively quickly on demand as needed without the expensive pleating rollers that create regular parallel folds in a sheet stock material. Moreover, the converter and the stock material take up much less space than the wrapping dunnage product produced therefrom.

Figure 1:
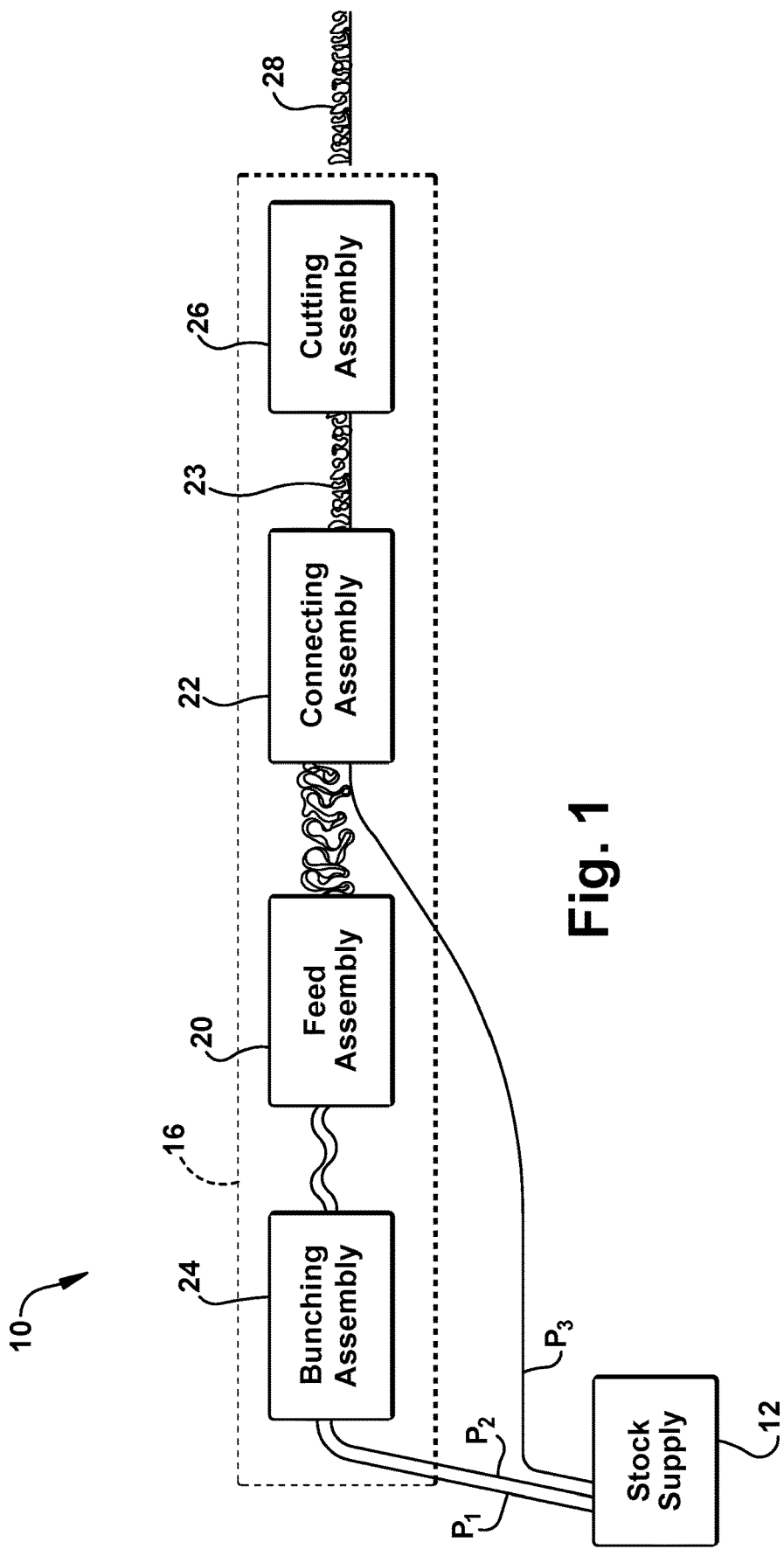
FIG. 1 is a schematic representation of an exemplary dunnage conversion machine provided in accordance with the present invention.
Figure 2:
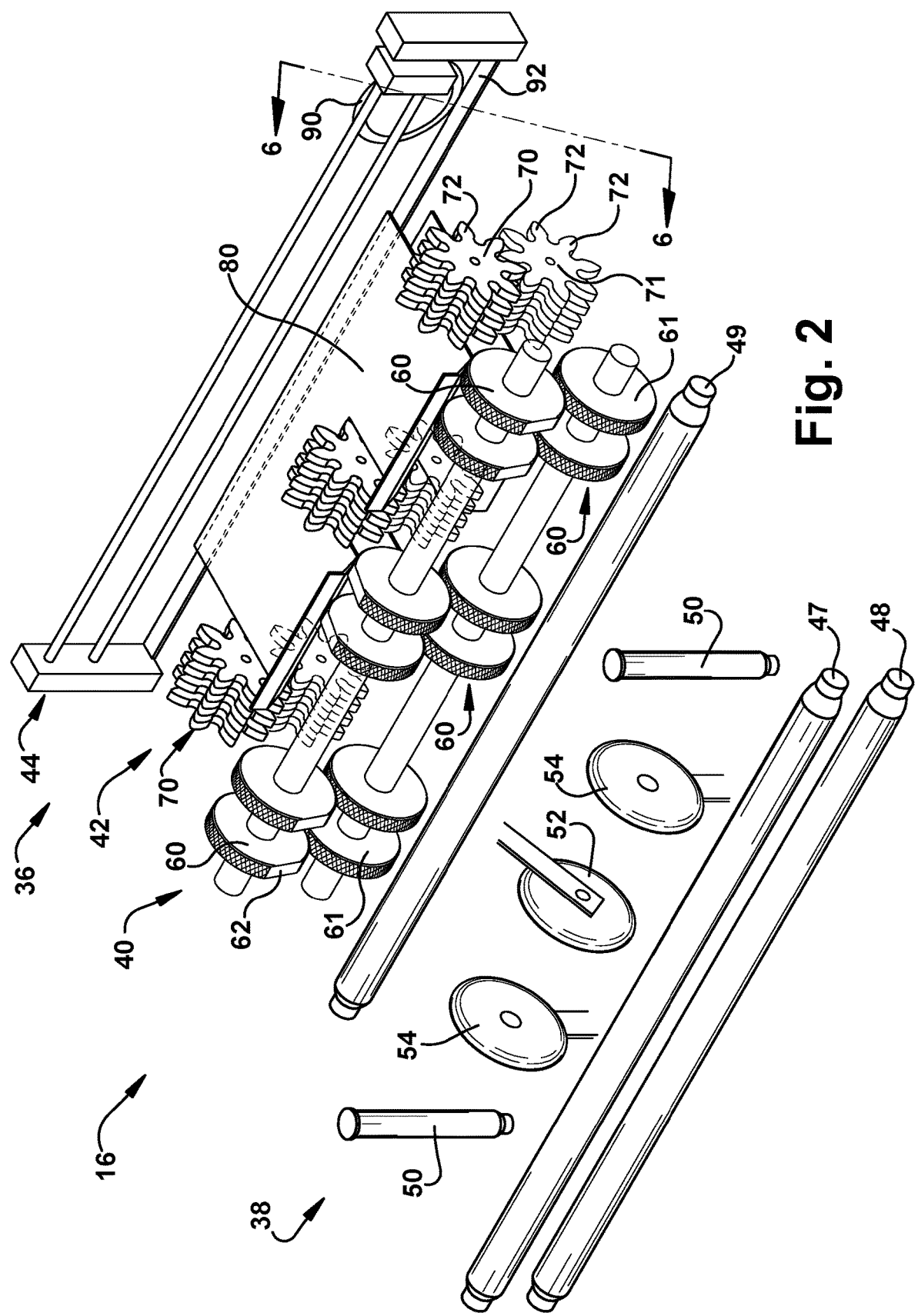
FIG. 2 is a schematic perspective view of operative elements of an exemplary dunnage conversion machine provided in accordance with the present invention.
Figure 3:
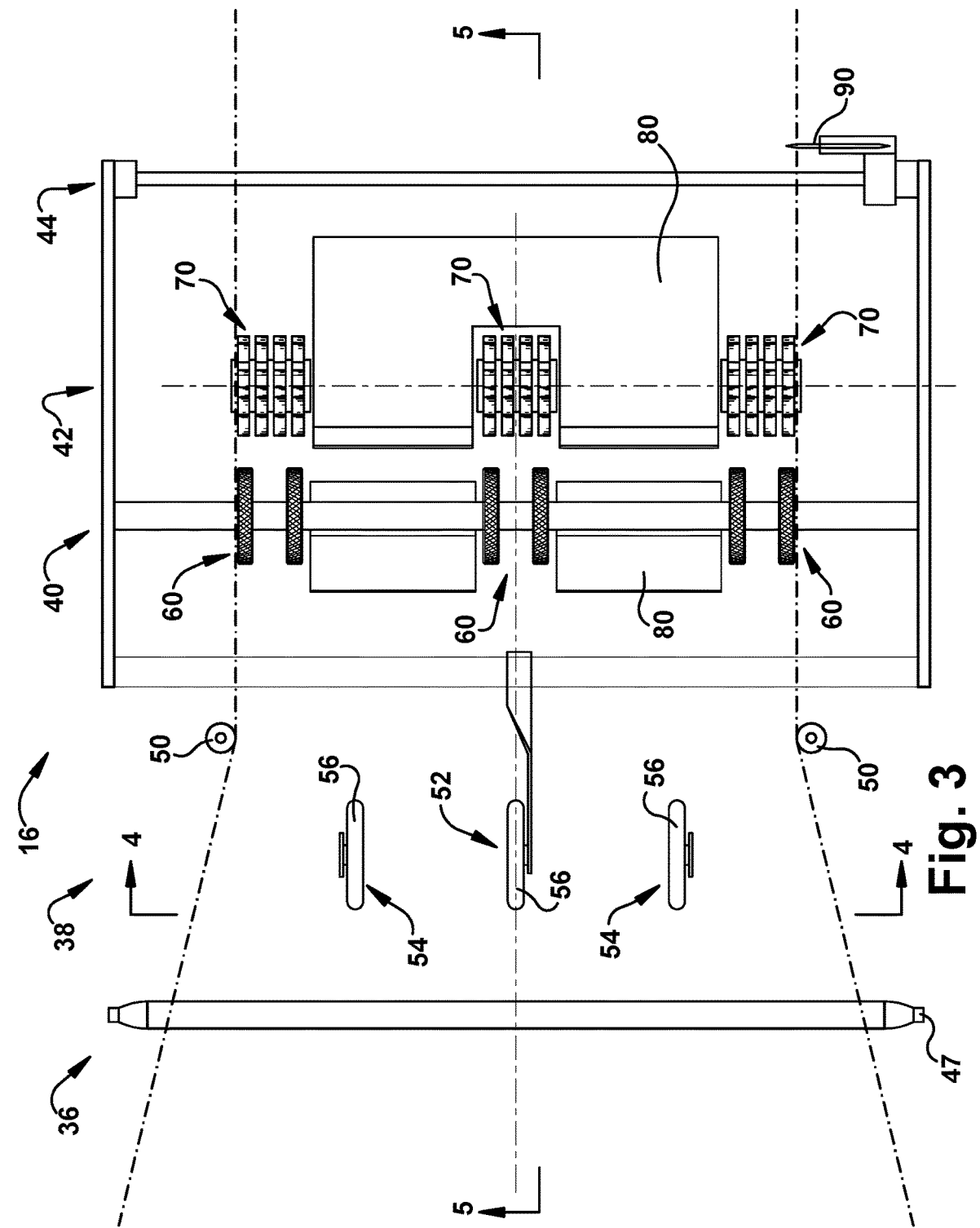
FIG. 3 is a top view of the dunnage conversion machine shown in FIG. 2.
Figure 4:
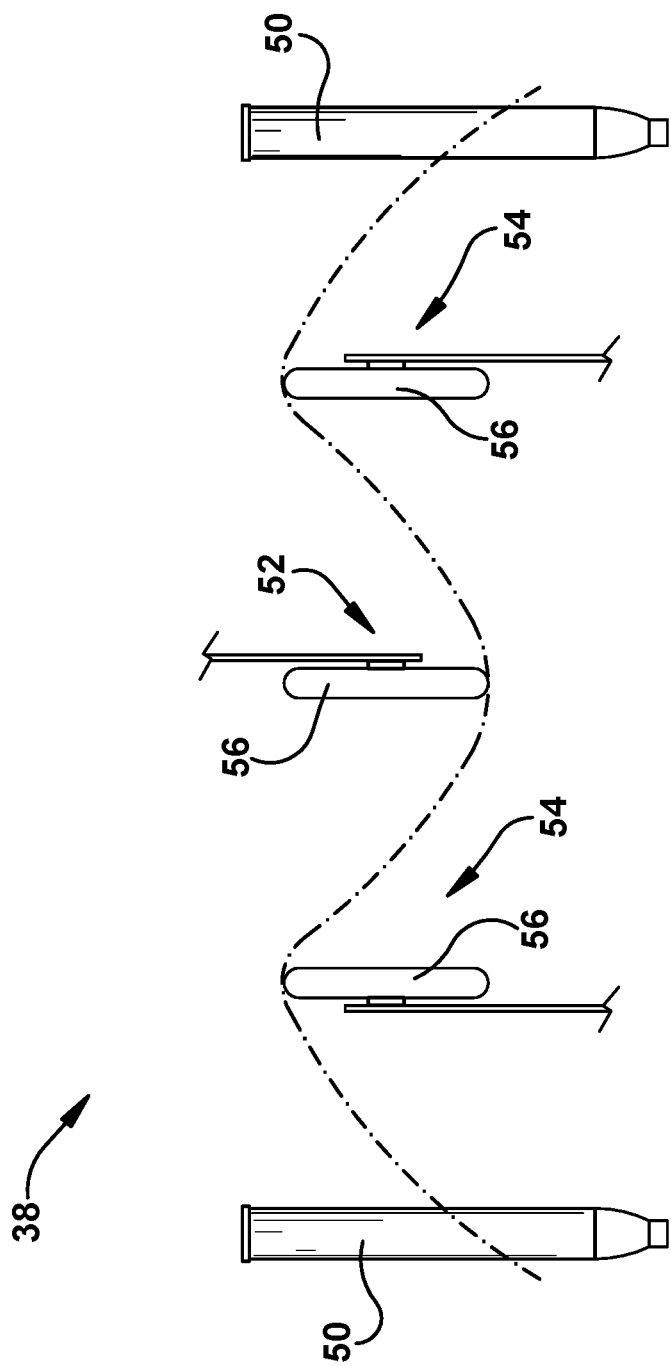
FIG. 4 is a cross-sectional view of the dunnage conversion machine shown in FIG. 3, looking downstream as seen along lines 4-4.
Figure 5:
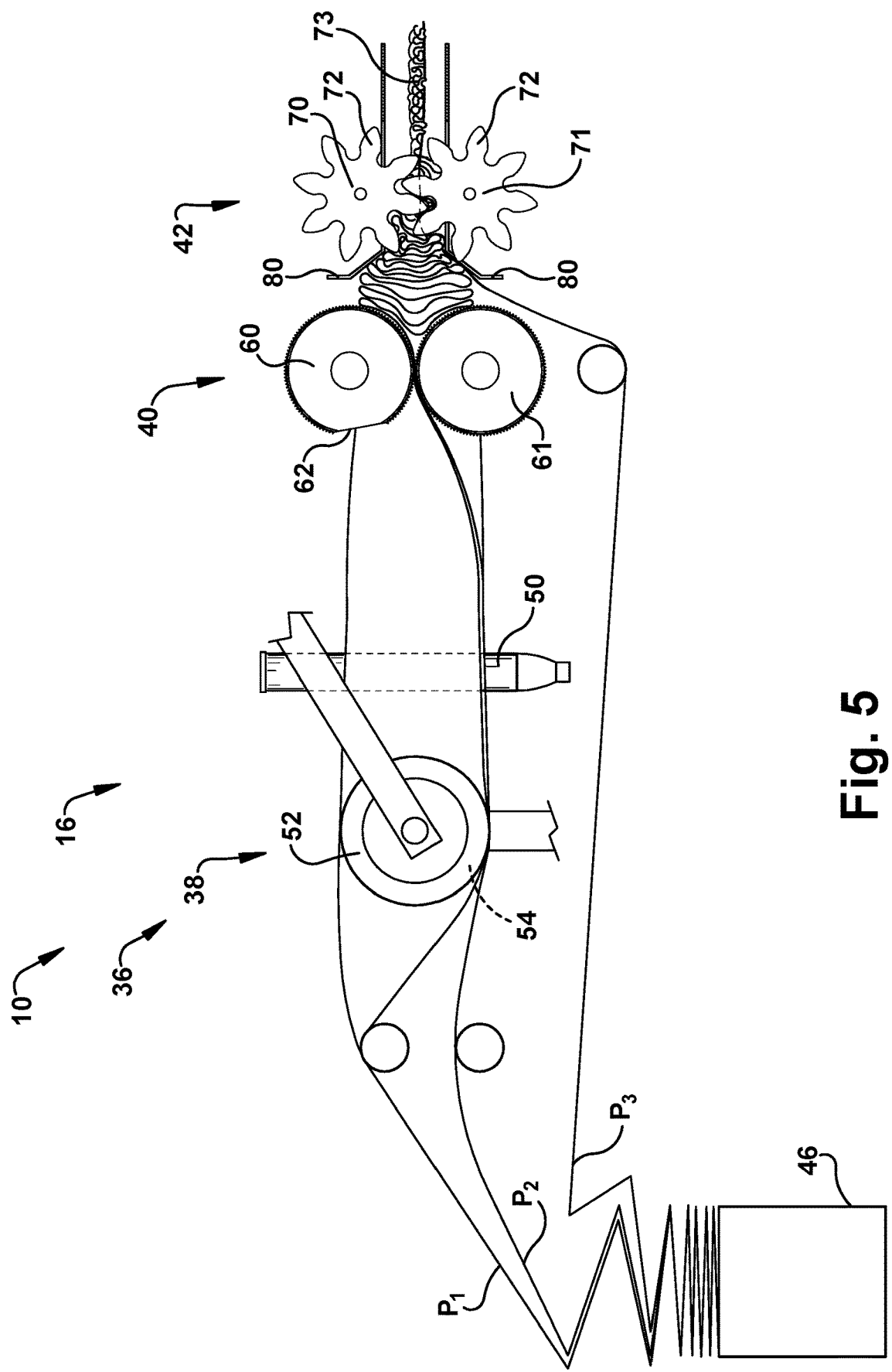
FIG. 5 is a cross-sectional side view of the dunnage conversion machine shown in FIG. 3, as seen along lines 5-5.
Figure 6:
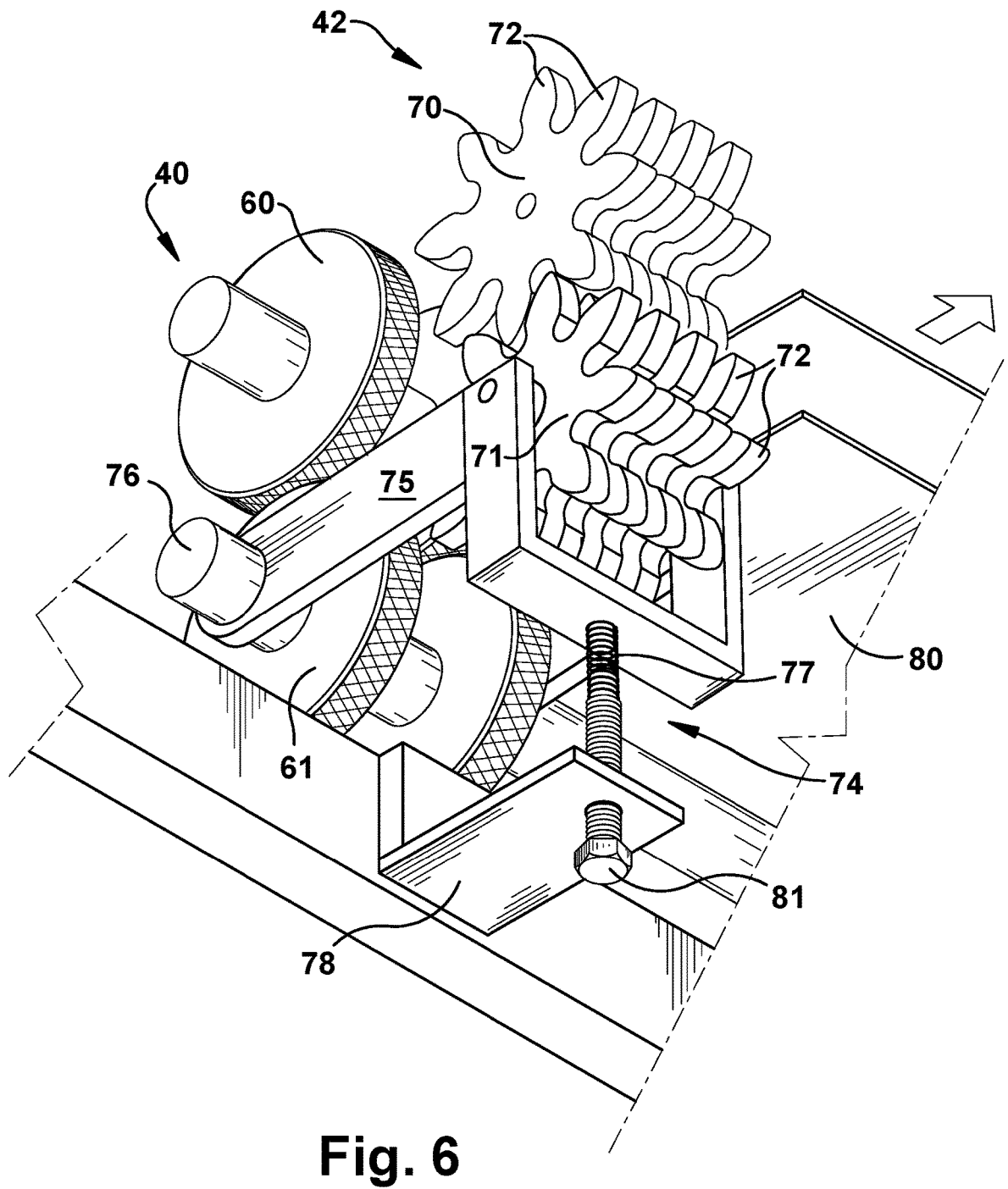
FIG. 6 is a cross-sectional end view of the dunnage conversion machine shown in FIG. 2, looking upstream as seen along lines 6-6.

Referring now to FIG. 1, an exemplary dunnage conversion system 10 provided by the invention includes a supply 12 of multiple webs of sheet stock material and a conversion machine 16 that converts the stock material into a wrapping dunnage product. A suitable sheet stock material includes paper and/or plastic sheets, supplied as a roll or a fan-folded stack, for example. An exemplary sheet stock material for use in the conversion machine 16 includes either a single ply or a multi-ply kraft paper provided either in roll form or as a series of connected rectangular pages in a fan-folded stack. Multiple rolls or stacks may be used to provide the multiple sheets or webs of stock material for conversion to the multi-ply dunnage product.

The dunnage conversion machine 16 includes a feed mechanism 20 for advancing at least one first sheet or web of stock material therethrough, and a connecting mechanism 22 for connecting multiple overlapping sheets together downstream of the feed mechanism 20. By passing the stock material at a slower rate than the feed mechanism 20 advances the stock material thereto, the connecting mechanism 22 retards the passage of the sheet stock material therethrough, which causes the stock material to randomly longitudinally crumple or fold in a confined space extending longitudinally between the feed mechanism 20 and the connecting mechanism 22.

The connecting mechanism 22 connects multiple overlying sheets of the stock material, including connecting at least one crumpled first sheet to one side of another or second sheet, to form a crumpled strip of dunnage 23. The second sheet may be a crumpled sheet that also passes through the feed mechanism 20 or an uncrumpled sheet that bypasses the feed mechanism 20. The conversion machine also may include a bunching assembly 24 to inwardly gather the sheet stock material upstream of the feed mechanism 20 and/or a cutting mechanism 26 downstream of the connecting mechanism 22 to sever discrete dunnage products 28 from the strip 23 of connected sheets.

In some situations the cutting mechanism 26 can be omitted altogether, such as when discrete lengths of sheet stock material are supplied to the feed mechanism 20 and the connecting mechanism 22. Another alternative is to employ a sheet stock material that is perforated across its width so that a length of wrapping dunnage can be torn from the strip of dunnage. The perforations can be formed in the stock material before being supplied to the conversion machine 16 or formed as part of the conversion process. Additionally, the conversion machine 16 can automatically separate a desired length of wrapping dunnage from a strip of dunnage made of perforated stock material. This can be accomplished by stopping the feed mechanism 20 to hold an upstream portion of the sheet stock material while the connecting mechanism 22 continues to feed the stock material therethrough. As a result, the stock material will automatically separate at a line of perforations located between the feed mechanism 20 and the connecting mechanism 22.

Referring now to FIGS. 2-5, further details of an exemplary conversion machine 36 are shown. Following a path of the stock material as it moves downstream through each component of the conversion machine 36, the conversion machine 36 includes a bunching assembly 38, a feed assembly or mechanism 40, a connecting assembly or mechanism 42, and a cutting assembly or mechanism 44. The feed mechanism 40 draws one or more first sheets of stock material from a supply 46 (FIG. 5), over one or more bars or rollers 47, 48, and 49 that guide each sheet through or around the bunching assembly 38.

The bunching assembly 38 laterally inwardly gathers the one or more sheets passing therethrough. This inward gathering can prevent or minimize tearing of the stock material and promote loft as the stock material is fed into the feed mechanism 40. The illustrated bunching assembly 38 includes lateral guides 50 that extend transverse the thickness of the stock material, generally upright in the illustrated orientation. The lateral guides 50 are laterally spaced on opposing sides of the path of the sheet stock material, for example at a distance that is less than the width of the sheet, to reduce the width of the stock material.

The illustrated bunching assembly 38 also includes upper and lower guide members 52 and 54, which in the illustrated embodiment include guide wheels 56 that bear against the stock material. The upper and lower guide members 52 and 54 are laterally-spaced and transversely offset from one another. The guide members 52 and 54 extend into the path of the sheet stock material alternately from above and from below at locations spaced across the width of the path, causing the stock material to transversely undulate therebetween (see FIG. 4). The bunching assembly 38 thus gathers or bunches a greater quantity of sheet stock material toward the center of the path, which may lead to lateral crumpling as the sheet or sheets subsequently pass through the feed mechanism 40. Lateral crumpling can create fold lines approximately parallel to a longitudinal dimension of the stock material (generally parallel to the path of the stock material) and/or an interruption of the lateral fold lines created by longitudinal crumpling between the feed mechanism 40 and the connecting mechanism 42 as described below. The lateral and longitudinal crumpling of the sheet stock material is believed to enhance the cushioning properties of the dunnage product. The spacing between the lateral guides 50 also can be adjustable to accommodate different widths of the stock material or to vary the amount of gathering or bunching. The bunching assembly 38 can be omitted or placed between the feed mechanism 40 and the connecting mechanism 42 in alternative embodiments.

From the bunching assembly 38, the inwardly-drawn stock material passes to the feed mechanism 40. The illustrated feed mechanism 40 includes at least two rotating feed members 60 and 61 for advancing the sheet stock material therebetween. The feed members 60 and 61 have a surface that provides sufficient friction to grip the stock material, and may be knurled or have a rubber or other high-friction surface, for example, to provide the desired grip on the stock material. The feed mechanism 40 can include one pair of rotating members, a single rotating member on one side of the sheet stock material and multiple rotating members on the other side of the stock material, or as shown, multiple laterally-spaced pairs of rotating members 60 and 61 for advancing the sheet stock material therethrough. The opposing rotating members 60 and 61 in each pair preferably, but not necessarily, are biased against one another to maintain a grip on the sheet stock material passing therebetween. The illustrated rotating members are mounted on a common shaft, however, each pair of the rotating members 60 and 61 may be independently biased toward each other, similar to the arrangement described with respect to the connecting mechanism 36 in the following paragraphs.

The rotating members 60 and 61 additionally can have portions that allow the stock material to periodically slip relative to the rotating members 60 and 61. This relative slip can be accomplished, for example, by providing flat portions 62 on the illustrated rotating members 60 and 61. If these flat portions 62 are circumferentially spaced at laterally spaced locations across the width of the stock material, a lateral shifting or twisting motion can be imparted to the stock material to cause differential lateral crumpling between the rotating members 60 and 61 and a longitudinal space between the feed mechanism 40 and the connecting mechanism 42.

The connecting mechanism 42 receives the stock material from the feed mechanism 40, and optionally also may receive one or more sheets that bypass the feed mechanism 40 to provide an uncrumpled backing and/or cover sheet or sheets. The illustrated connecting mechanism 42 includes at least two rotating gear members 70 and 71 having interlaced teeth for deforming the sheet stock material passing therebetween, thereby mechanically interlocking multiple layers and multiple overlapping sheets along lines of connection to hold them together as a connected strip of dunnage. This mechanical connection is distinguished from a chemical or adhesive bond between the layers. The gear members 70 and 71 flatten, crease, fold, and/or punch the stock material as it passes therebetween. Although the connecting mechanism 42 includes at least two rotating gear members 70 and 71 between which the stock material is fed, more gear members may be employed in various configurations, as described with respect to the feed members 60 and 61. Thus the gear members 70 and 71 may include a single gear stretching across the width of the stock material opposed by another gear, or one or more gears opposing the single gear at laterally-spaced positions, or the illustrated plurality of laterally-spaced pairs of opposed gears 70 and 71.

The rotating gear members 70 and 71 are driven at a rate that is less than the rate that the feed mechanism 40 advances the sheet stock material thereto. In an exemplary embodiment each pair of connecting gears 70 and 71 includes a biasing member 74 that biases one gear 70 toward an opposing gear 71 and thereby provides an adjustable pinch pressure between each pair of gears. Accordingly, if more tension is needed at a particular location, for example toward an outer edge of the sheet stock material, selected gears may have their pinch pressure adjusted to effect the desired quality or character of the connection between the multiple sheets passing therebetween.

Thus in the illustrated embodiment the gear members 71 on one side of the path are supported by pivot shafts 75 pivotally connected to a corresponding axle 76 of the feed mechanism 40. Each gear member 71 is biased toward the opposing gear member 70 by a biasing device 74 that includes a spring 77. The spring 77 is interposed between a fixed frame member 78 and a yoke 79 connected to the gear member 71 and the pivot shafts 75. A bolt 81 axially aligned with and on one side of the spring 77 is threadably mounted to the frame member 78 to allow for adjustment of the biasing force applied by the spring 77. Because each of the gear members 77 is independently supported and biased toward the opposing gear member 70, differential pinch pressure may be applied at locations spaced across the width of the stock material. The present invention is not limited to the illustrated structure, however, and equivalent biasing devices may be employed to provide independent adjustability at different locations as the stock material passes through the connecting mechanism 42.

Guide chute or tunnel elements 80 constrain the movement of the stock material passing between the feed mechanism 40 and the connecting mechanism 42 to cause the stock material driven therebetween to randomly crumple within the restricted longitudinal space defined by the walls of the tunnel 80, the feed mechanism 40 and the connecting mechanism 42. Longitudinal crumpling creates fold lines extending approximately transverse the longitudinal dimension of the stock material, which generally is perpendicular to the path of the stock material through the machine 36. When longitudinal crumpling is combined with crumpling action caused by the inward bunching of the bunching assembly 38 and any lateral twisting or shifting caused by the feed mechanism 40, the sheet stock material is randomly crumpled, creating fold lines with random lengths and orientations, and an irregular pitch between the folds.

To connect one or more uncrumpled sheets of stock material to the crumpled sheet or sheets, the dunnage converter 36 can provide a bypass path for an uncrumpled sheet or sheets to bypass the feed mechanism 40 and join with the crumpled sheet or sheets at the connecting mechanism 42. The connecting mechanism 42 then connects the uncrumpled sheet or sheets to the crumpled sheet or sheets. To that end a bypass guide member, such as a guide bar or roller 49, may be provided to guide the uncrumpled sheet or sheets around the bunching assembly 38 and/or the feed mechanism 40 to the connecting mechanism 42. A corresponding guide bar or roller can be provided on an opposing side of the feed mechanism 40 to direct one or more additional uncrumpled sheets around the feed mechanism 40 to be secured to an opposing side of the one or more crumpled sheets by the connecting mechanism 42.

To obtain the desired length of dunnage products, the sheet stock material may be perforated across its width so that lengths of the finished products can be torn off as desired for use in wrapping an article or for layering inside a container. The perforations can be formed prior to the stock material being supplied to the conversion machine or formed as part of the conversion process, as noted above. A rotating perforating wheel, rotating in the direction of the stock material, can operate without stopping the conversion process. The perforations also can be formed to provide variable lengths of wrapping dunnage as needed. By stopping the feed mechanism 20 and continuing to drive the connecting mechanism 22, the machine 16 can burst the stock material at the perforations to separate a length of wrapping material from the strip of dunnage. The stock material alternatively may be pre-cut to form discrete sheets of the desired length, or as shown in the illustrated embodiment, the conversion machine 36 may include a cutting mechanism 44 downstream of the connecting mechanism 42 for cutting a desired length from the connected strip of dunnage 73.

An exemplary cutting mechanism 44 includes a rotatable cutting wheel 90 movable across the path of the sheet stock material and a stationary blade 92 against which the cutting wheel acts to cut the crumpled strip of dunnage 73 therebetween. Other cutting mechanisms may be used in place of or in addition to the illustrated cutting mechanism 44 to separate a dunnage product 100 from the connected strip 73.

The feed mechanism 40 and the connecting mechanism 42 may be enclosed partially or completely within a housing (not shown). In which case, to facilitate loading a new supply of stock material into the conversion machine 16 or for maintenance, the housing may be openable to access the feed mechanism 40 and the connecting mechanism 42. In fact, one of the upper or lower rotating members 60 and 61 of the feed mechanism 40 and the respective upper or lower gear member 70 and 71 of the connecting mechanism 42 may be connected to an openable portion of the housing to separate the rotating members 60 and 61 and separate the gear members 70 and 71 to facilitate access to the path of the stock material through the conversion machine 16 along which it is converted into a dunnage product 100.

Figure 7:
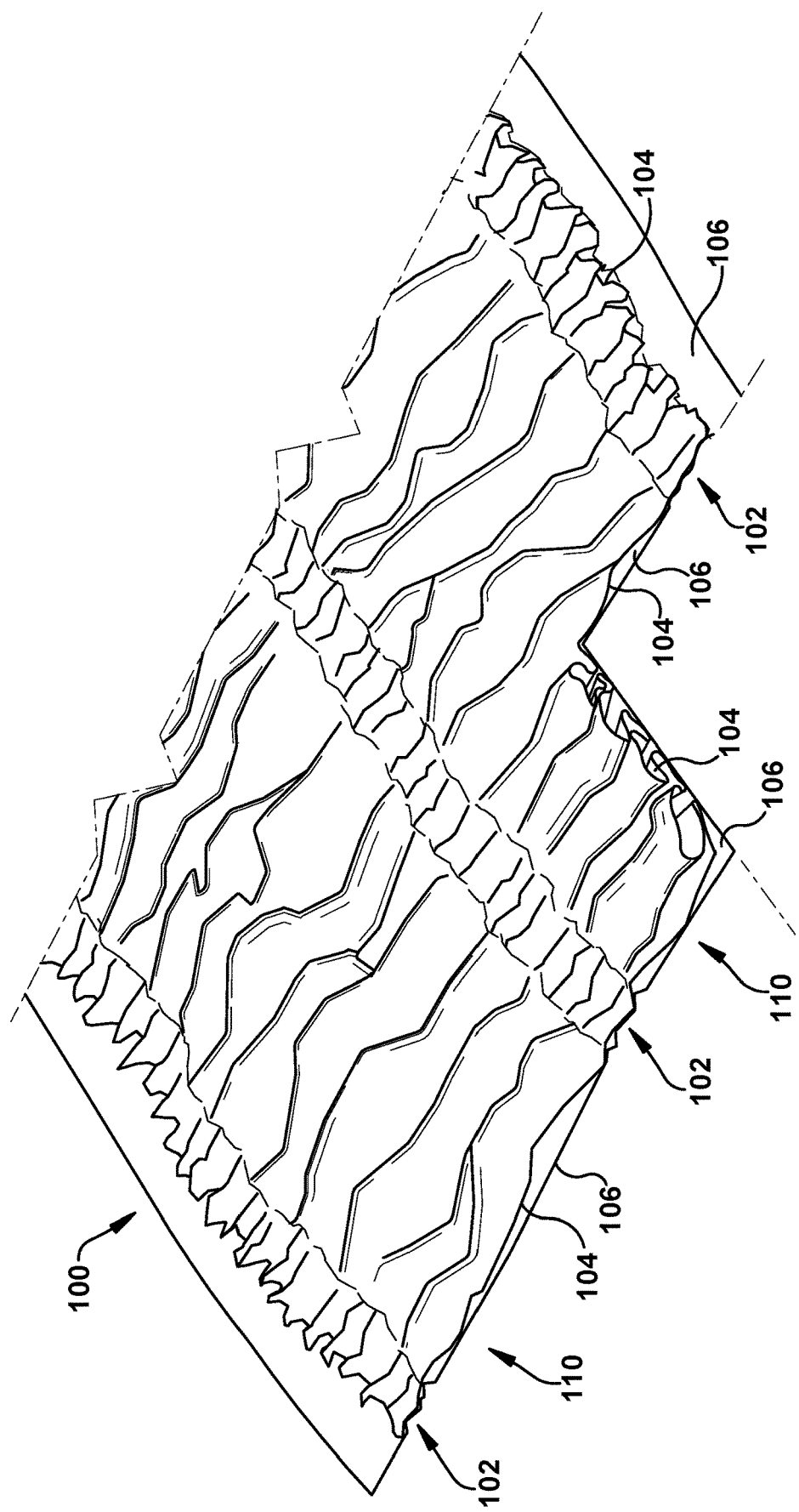
FIG. 7 is a schematic view of a dunnage product produced by the dunnage conversion machine shown in FIG. 3.

The resulting dunnage product 100, shown in FIG. 7, includes at least one, and preferably a plurality, of laterally-spaced, longitudinally-extending connecting bands 102 where the sheet stock material is embossed or pierced or punched or otherwise connected to hold multiple plies 104 and 106 of stock material together. The stock material generally is compressed in these connecting bands 102 and thus the crumpled plies 104 provide relatively greater loft in cushioning regions 110 outside the connecting bands 102.

In a wrapping product that has an uncrumpled ply 106, the uncrumpled ply acts as a carrier for the crumpled ply. If the same width of stock material is used for the uncrumpled ply 106 and the one or more crumpled plies 104, the crumpling process generally will reduce the width of the crumpled ply or plies 104 such that the uncrumpled carrier ply 106 will extend laterally beyond the laterally-outer edges of the crumpled ply or plies 104. These laterally-outer portions also may be folded inwardly into the connecting bands 102 before or after being connected to further stiffen the dunnage product lengthwise, provide a more consistent finished edge and/or to improve the quality of the connection between the multiple layers of stock material.

Additionally, if more than one uncrumpled ply 106 is desired, the additional uncrumpled sheet or sheets may be fed into the connecting mechanism 36 (FIG. 2) on the same side or on opposing sides of the crumpled sheet or sheets. The random crumpling of the crumpled ply or plies 104 and the laterally-spaced connecting bands 102 holding the uncrumpled ply or plies 106 to the crumpled ply or plies 104 provides a high quality dunnage product.

Changing the number of crumpled sheets, the weight of the stock material employed, or the use of either a crumpled or an uncrumpled carrier sheet can be used to vary the cushioning or other properties of the wrapping product. Cushioning properties also can be controlled by changing a ratio of the feed rate of the stock material through the feed mechanism 40 and the connecting mechanism 42. Adjusting the gap between laterally-spaced bunching guides also can change the final wrapping product.

Referring back to FIG. 5 for a moment, in an exemplary operation multiple sheets $P_1$, $P_2$ and $P_3$ of stock material are fed from the supply 46, at least one sheet, and in the illustrated embodiment two sheets $P_1$ and $P_2$, are laterally-inwardly bunched in the bunching assembly 38 and advanced by the feed mechanism 40 through the pulling feed wheels 60 and 61 toward the connecting gears 70 and 71. Because the connecting mechanism 42 rotates the gears 70 and 71 at a slower rate than the feed wheels 60 and 61, the stock material will longitudinally bunch up in the tunnel 80 connecting the two, thereby creating random crumples or folds in the stock material. The connecting mechanism 42 pulls the crumpled sheets $P_1$ and $P_2$ of stock material therebetween, along with an uncrumpled carrier sheet $P_3$, if any, that bypassed the feed mechanism 40, and connects the multiple sheets $P_1$, $P_2$ and $P_3$ together as the overlying plies pass between the connecting gears 70 and 71. Finally, if a cutting mechanism 44 is employed, a desired length of dunnage is cut from the connected strip 73 of dunnage to provide a dunnage product 100 (FIG. 7) with the desired length.

In operation, paper or other sheet stock material $P_1$, $P_2$, and $P_3$ flows from a supply 12 thereof, for example from a roll or a stack, through a bunching assembly 24. In this assembly, the stock material is bunched toward the center so as to reduce the width of the web of stock material. In the feed mechanism 20, a series of rollers or wheels feed the inwardly-bunched stock material toward a connecting mechanism 22. These feed wheels rotate faster than gears in the connecting mechanism 22, however, thereby retarding the advance of the stock material and causing the stock material to randomly longitudinally fold, crumple, and/or roll. Unlike the shapes formed between pleating rollers, however, the crumpled folds formed during the crumpling operation are irregular and randomly oriented, although generally falling within a range of widths or lengths. The height or width of the folds or crumpled portions can be controlled by adjusting the gap between the bunching guides. As the stock material is fed through the feed and connecting mechanisms 20 and 22, the crumpled folds are creased, crimped, or otherwise fixed along relatively narrow lines of connection to maintain their crumpled nature and provide loft in the dunnage product. This action forms the finished dunnage product, which then can be cut to a desired length.

In summary, a dunnage conversion machine 36 converts a sheet stock material into a dunnage product that is relatively thicker and less dense than the stock material, but is relatively thin and sufficiently flexible to function as a protective wrap. The conversion machine 36 includes a feed mechanism 40 that advances a sheet stock material therethrough and a connecting mechanism 42 downstream of the feed mechanism 40. The connecting mechanism 42 retards the passage of the sheet stock material therethrough by feeding the stock material therethrough at a slower rate than the feed mechanism 40 feeds the stock material to the connecting mechanism 42. This causes the stock material to randomly crumple in a longitudinal space between the feed mechanism 40 and the connecting mechanism 42. The connecting mechanism 42 connects multiple overlapping layers of sheet stock material together as they pass therethrough, including connecting at least one crumpled sheet to one side of one other sheet. The other sheet can be advanced through the feed mechanism 40 and crumpled, or guided around the feed mechanism 40 to the connecting mechanism 42 to be connected to the crumpled sheet or sheets.

Alternative Wrappable Dunnage Converter

Figure 8:
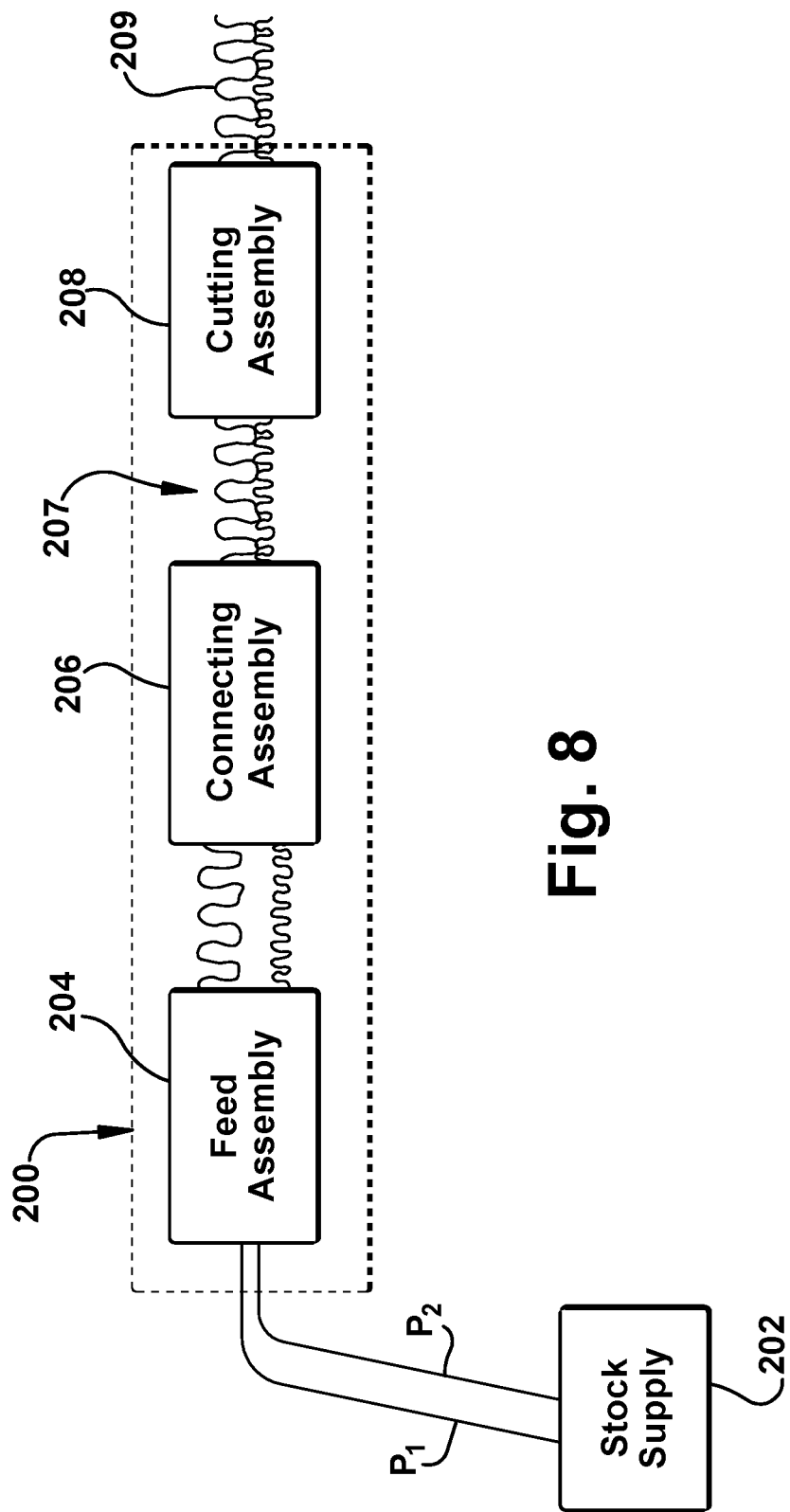
FIG. 8 is a schematic representation of another dunnage conversion machine provided in accordance with the present invention.
Figure 9:
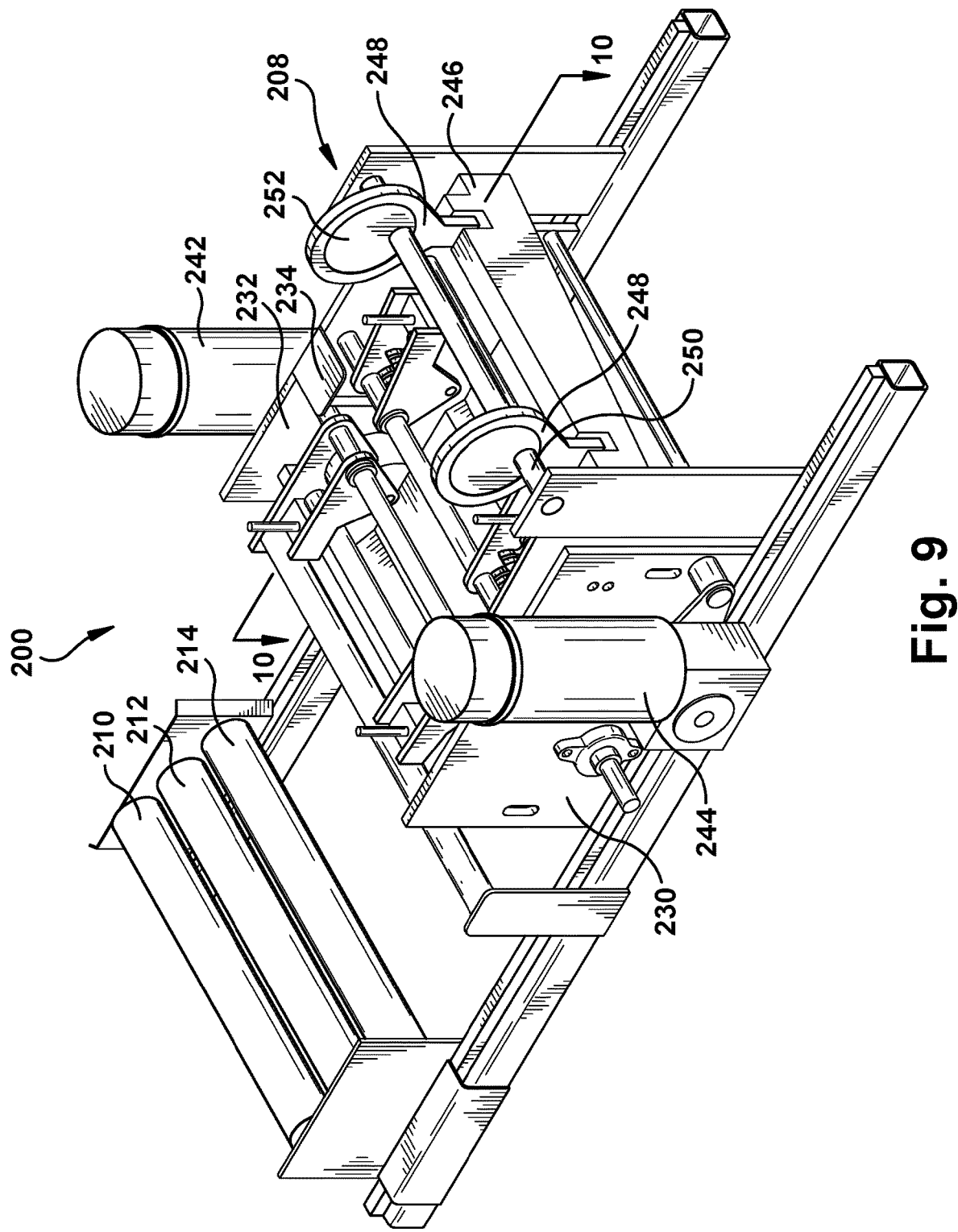
FIG. 9 is a perspective view of an exemplary dunnage conversion machine consistent with the schematic representation in FIG. 8.
Figure 10:
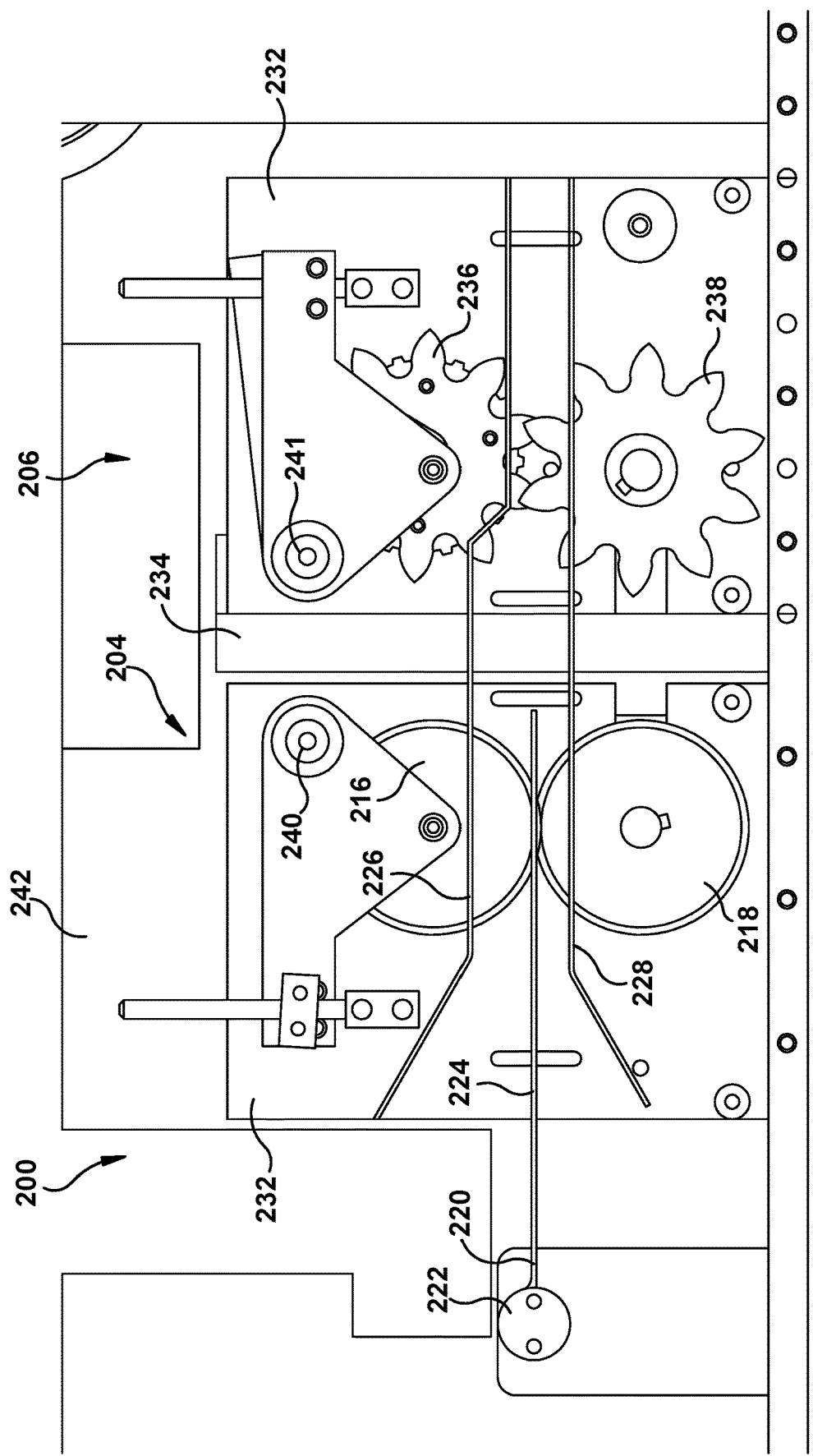
FIG. 10 is a cross-sectional elevation view of a portion of the dunnage conversion machine of FIG. 9 as seen generally along lines 10-10 in FIG. 9.

FIGS. 8-10 show another embodiment of a dunnage conversion machine 200 provided in accordance with the present invention. The conversion machine 200 converts a sheet stock material into a wrapping dunnage product, and includes a supply of sheet stock material 202, a feed assembly 204 that draws multiple plies $P_1$ and $P_2$ of sheet stock material from the supply, and a connecting assembly 206 that connects the plies together to form a strip of dunnage 207. The connecting assembly 206 passes the plies or sheets of stock material therethrough at a slower rate than the rate at which the plies are fed from the feed assembly 204, thereby cooperating with the feed assembly 204 to cause the stock material to randomly crumple between the feed assembly 204 and the connecting assembly 206. A cutting assembly 208 downstream of the connecting assembly 206 severs discrete lengths of a wrapping dunnage product 209 from the strip 207. These components similar to the corresponding components of the preceding embodiment, except as noted. For example, the illustrated conversion machine 200 does not employ the bunching assembly 38 (FIG. 1) of the previous embodiment.

Between the supply 202 and the feed assembly 204, the conversion machine 200 includes a series of three bars or rollers 210, 212, and 214 with axes that are aligned in parallel and in a common plane that is inclined relative to the downstream direction. These rollers 210, 212, and 214 define a serpentine path for the sheet stock material as it travels from the stock supply 202 to the feed assembly 204. These rollers can be used in conjunction with a fan-fold supply of sheet stock material to provide a relatively consistent tension on the stock material coming from the supply or supplies, particularly when the supply includes a fan-folded stock material. The rollers also provide better tracking, so that the stock material enters the feed assembly 204 in a more consistent lateral location.

The illustrated conversion machine 200 produces an at least two-ply wrapping dunnage product 209. After the serpentine rollers 210, 212, and 214, both plies $P_1$ and $P_2$ enter the feed assembly 204. As in the previous embodiment, the feed assembly 204 includes upper and lower rotating member 216 and 218 that form pairs of laterally-spaced rotating members, in this case wheels. The alternative arrangements described above also can employed in this embodiment. The upper rotating members 216 engage and advance an upper ply of sheet material and the lower rotating members 218 engage and advance a lower ply of sheet material. The rotating members 216 and 218 in this embodiment are mounted on common laterally-extending shafts, and the upper rotating members 216 are pivotably mounted and biased against the lower rotating members 218.

At an upstream end of the feed assembly 204 at least one ply is separated from at least one other ply. Typically only two plies P1 and P2 are used, and the two plies follow different paths into the feed assembly 204. This is accomplished with a separator 220 having a round upstream end 222 and a plate member 224 extending therefrom in a downstream direction into the feed assembly 204 and between two pairs of laterally spaced-apart rotating members or wheels 216 and 218 that form part of the feed assembly 204. These rotating member pairs 216 and 218 are laterally spaced on opposite sides of the separator plate or engage one another through laterally-spaced openings in the separator plate.

Above and below the separator plate 224, upper and lower channel guide member 226 and 228 or channel guide plates define a path through the feed assembly 204 and the connecting assembly 206. These channel guides 226 and 228 define the upper and lower boundaries that confine the sheet stock material therein to facilitate the crumpling of the stock material between the feed assembly 204 and the slower speed connecting assembly 206. The sides of this pathway are bounded by opposing laterally-spaced frame members 230 and 232, which also support the transverse shafts of the feed assembly 204 and the connecting assembly 206 in this embodiment. In addition, the separator plate 224 generally is parallel to the upper and lower guide members 226 and 228, but is closer to one of the guide members. Consequently, the stock material passes on either side of, in this case above and below the separator plate 224, whereby the stock material on either side will fold and crumple asymmetrically. This asymmetrical folding and crumpling yields two different crumpled sheets generally having waveforms with independent frequencies and amplitudes in the irregular crumpling of the sheet material. Accordingly, the different size ply in-feed chambers or passages defined by the channel guides 226 and 228 and the separator plate 224 allow the plies to randomly crumple with different frequencies and amplitudes so the plies are less likely to interlock when they are brought together, thereby providing more loft after the plies are connected. Without the separator plate 224, the plies would nest into each other to create a thinner, less supportive dunnage product.

After the feed assembly 204, the separator plate 224 ends and the upper and lower channel guide plates 226 and 228 converge adjacent the conversion assembly 206. This causes the separate plies to come together and become connected to one another as they pass through the connecting assembly 206 together. And while the upper and lower channel guides 226 and 228 define a converging space at the upstream side of the connecting assembly 206, the channel guides do not have to converge and can continue straight, all the way through the connecting assembly 206 without reducing the volume of the passage for the stock material.

Although this embodiment lacks the bunching assembly 38 (FIG. 1) of the previous embodiment, the illustrated conversion machine 204 includes laterally spaced-apart forming plow 234 between the feed assembly 204 and the connecting assembly 206 that reduce the width of the stock material and inwardly fold the free lateral edges as the stock material passes thereby. The forming plows 234 each have a curved surface that is mounted to extend into the path of the lateral edges of the stock material, gradually protruding further inward toward a downstream end thereof. As the lateral edges of the stock material are folded or turned inwardly by the lateral plows 234, the edges of the stock material of one layer can fold around and enclose the edges of the other layer, and the connecting assembly 206 then mechanically connects the overlapping layers together. This makes the lateral edges of the finished dunnage product more uniform, and the additional folding and the resulting additional layers passing through the connecting assembly 206 to form the connecting lines helps to hold the dunnage product together better. The conversion machine 200 defined by this feed assembly 204 and connecting assembly 206 provides approximately 40-55% crimp loss. This means that the wrap dunnage product that is produced is approximately 40-55% shorter than the stock material that is used to produce it.

The connecting assembly 206, like the feed assembly 204, includes two pairs of laterally spaced-apart rotating gear members or gears 236 and 238 that are biased together and connect the overlapped layers of stock material as the stock material passes between the gears. Alternative arrangements described with respect to the previous embodiment also are contemplated for this embodiment. Upper gears 236 are biased against lower gears 238 by a biasing member, such as a spring. The biased rotating members 216, 218 of the feed assembly 204 and the biased gears 236 and 238 of the connecting assembly 206 are each mounted in a cantilever fashion for rotation about respective pivots 240 and 241 so that a smaller spring can be used to provide sufficient biasing force.

In the illustrated conversion machine 200, the feed assembly 204 and the connecting assembly 206 are driven by a common electric drive motor 242. The drive motor 242 positively drives the lower rotating members 218 of the feed assembly 204 and is connected to the lower gear members 238 of the connecting assembly 206 via a chain and suitable sprocket (not shown). The ratio of the speed between the rotating members 216 and 218 of the feed assembly 204 and the gears 236 and 238 of the connecting assembly 206 can readily be adjusted by adjusting the relative sizes of the sprockets and providing a suitable chain therebetween. Alternatively, separate motors can be provided to separately drive the feed assembly 204 and the connecting assembly 206. A transmission also may be provided instead of the illustrated chain drive, to provide the ability to change the relative speeds of the feed wheels 216 and 218 and the gears 236, 238 without interrupting their operation.

A separate cut motor 244 drives a guillotine-style cutting assembly which includes a cutting blade 246 that extends across the width of the path of the dunnage strip and has a pair of crank arms 248 aligned with the laterally-spaced rotating members 216 and 218 of the feed assembly 204 and the gears 236 and 238 of the connecting assembly 206 to positively drive the cutting blade 246 through the layers of crumpled stock material with the most force applied at the lines of connection. The crank arms 248 are connected to a common shaft 250 and rotate through a cycle defined by respective cams 252. As noted above, the stock material could be perforated so that a length of wrapping dunnage can be torn from the strip of dunnage.

Figure 11:
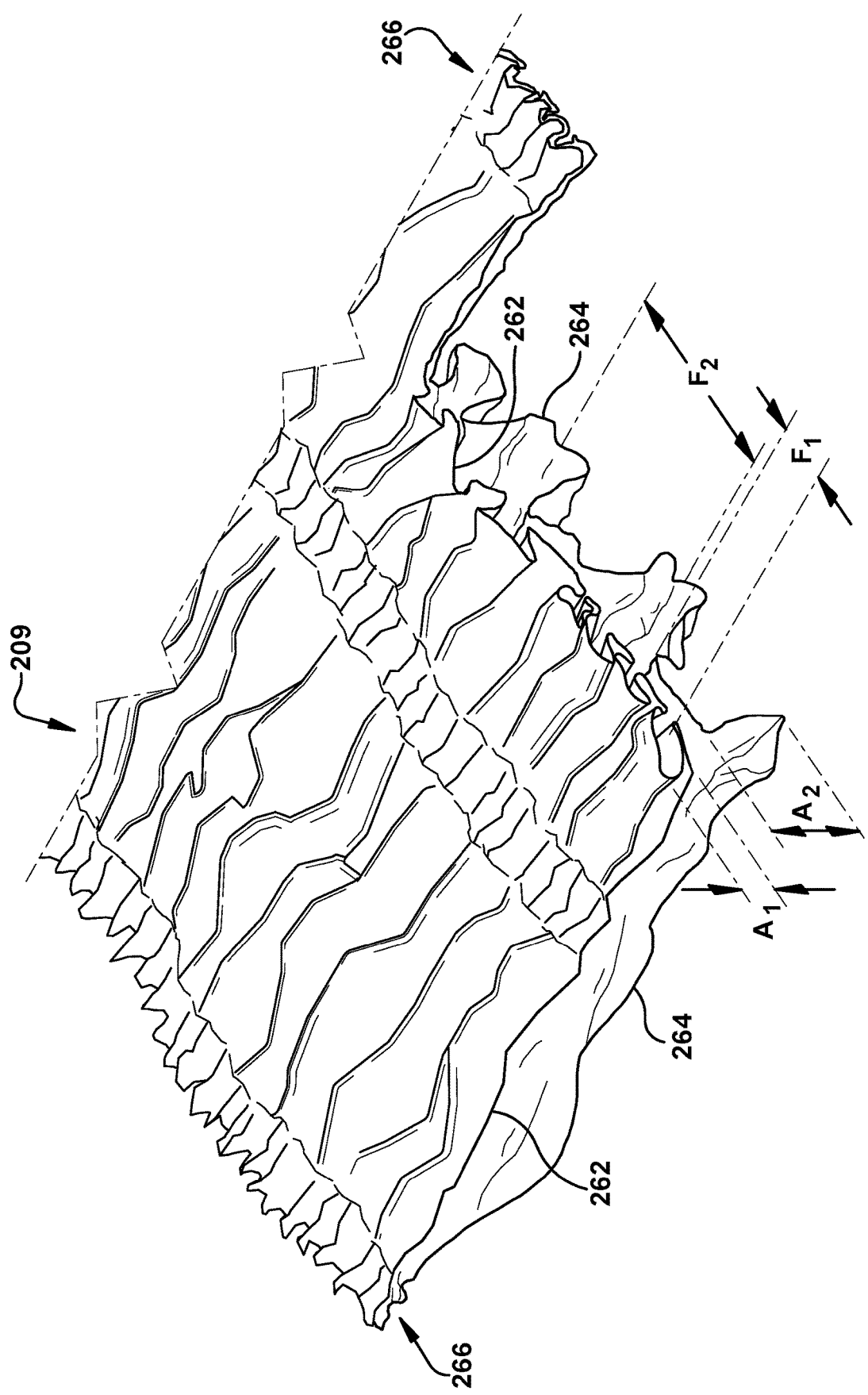
FIG. 11 is a schematic perspective view of a dunnage product produced by the dunnage conversion machine of FIG. 9.

As shown in FIG. 11, the resulting wrapping dunnage product 209 includes two plies 262 and 264 of randomly crumpled sheet stock material. Although the exact variation in the crumpled undulations is unpredictable, the amplitude and frequency of the undulations generally can be approximately predicted statistically, and is the result of the differential speed of the rotating members 216 and 218 of the feed assembly 204 and the gears 236 and 238 of the connecting assembly 206, and the size of the respective channels between the separator plate 224 and the channel guide plate 226 or 228 bounding the other side of the space through which a respective ply 262 or 264 travels (see FIG. 9). Because the gap is different on each side of the separator 220, the frequency $F_1$ and amplitude $A_1$ of the upper ply 262 relative to the frequency $F_2$ and the amplitude $A_2$ of the lower ply 264 generally are different. The differential crumpling keeps the two plies 262 and 264 from nesting with one another when they come together, thereby retaining loft in the resulting dunnage wrap 209.

Another Wrappable Dunnage Converter

Yet another exemplary dunnage conversion machine 300 is shown in FIGS. 12-15. This conversion machine is consistent with the schematic representation of the dunnage conversion machine 200 of FIG. 9. Unless specified, features of this conversion machine 300 are substantially similar or the same as those of one or both of the previous embodiments. While the basic operation of this conversion machine is similar to that described with regard to the previous two embodiments, this conversion machine includes several features that make it easier to load and less likely to jam.

Figure 12:
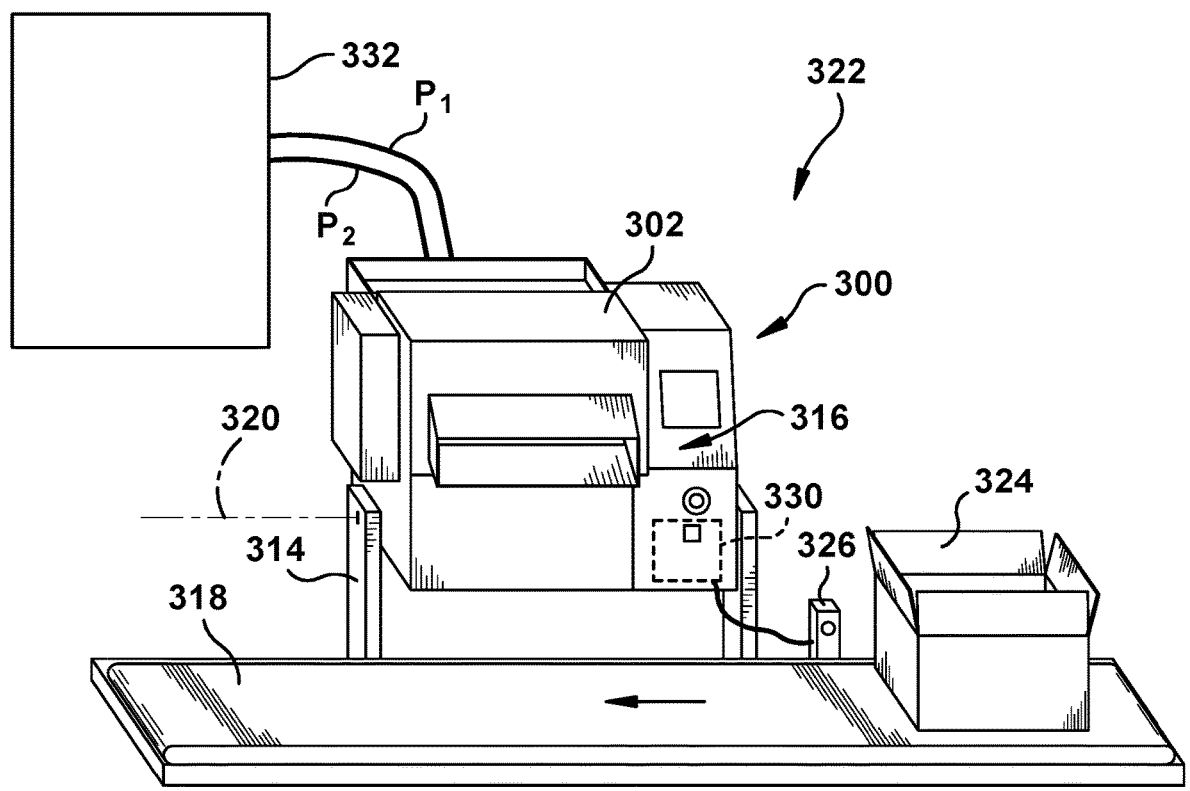
FIG. 12 is a schematic perspective view of a packaging system including yet another dunnage conversion machine.

An exemplary packaging system 322 shown in FIG. 12 includes the conversion machine 300, the conveyor 318 for transporting containers 324 to a packaging location adjacent the outlet 316, and a control sensor 326 mounted adjacent the conveyor 318 at a position upstream of the conversion machine 300. By measuring and/or inputting the conveyor speed, a controller 330 incorporated into the conversion machine 300 or remote from the conversion machine 300 can use a signal from the control sensor 326 to trigger a timer. The length of time from when the sensor 326 is triggered until a container 324 on the conveyor 318 is no longer sensed by the sensor 326 can be used to determine the length of the container 324 and thereby the length of an appropriate wrapping dunnage product. The controller 330 can automatically determine the appropriate length and control the conversion machine 300 to dispense the wrapping dunnage product directly to the container.

A suitable application for such a system 322 would arise when a wrapping dunnage product will be used as a bottom or top layer in the container. Consequently, the production of a wrapping dunnage product for layering in a container can be automated and a wrapping product of the appropriate length can be provided automatically and on demand in a more compact configuration than a pre-produced supply of wrapping dunnage material.

The conversion machine 300 generally includes a housing 302 that surrounds or incorporates both a conversion assembly that includes a feed assembly 304 and a connecting assembly 306, and a cutting assembly 306. The conversion machine 300 also includes the forming plows 312 between the feed assembly 304 and the connecting assembly 306 that were described with reference to the previous embodiment. The housing 302 is mounted to a stand 314 to raise an outlet 316 of the housing 302 above a packaging surface. In the illustrated embodiment the packaging surface includes a conveyor 318. The housing 302 is pivotable about an axis 320 to direct the wrapping product to output in a desired direction.

Figure 16:
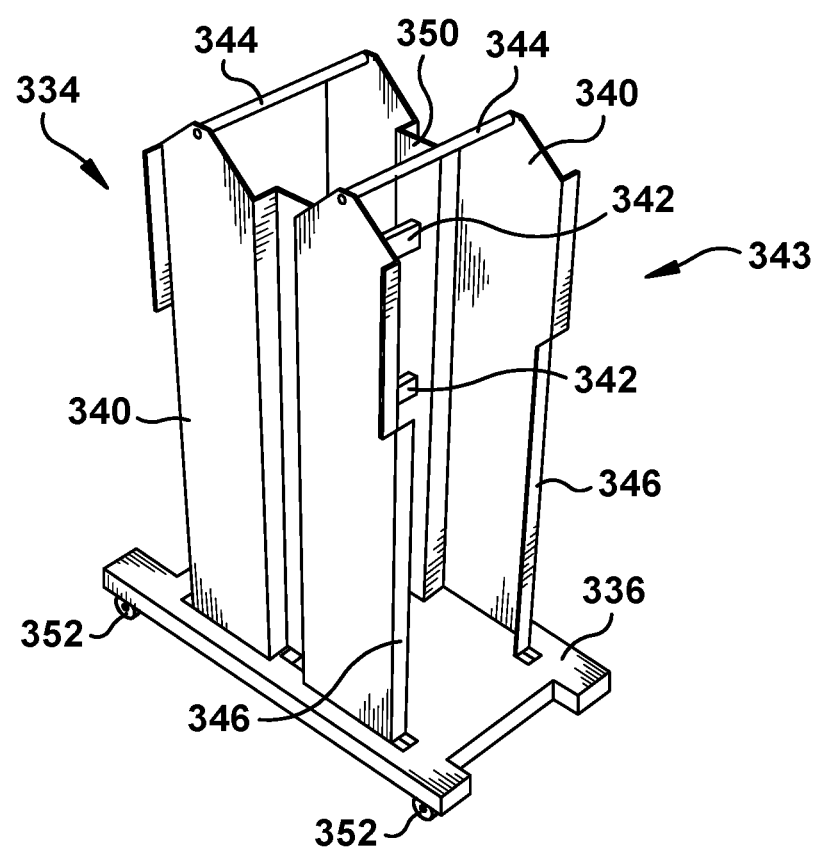
FIG. 16 is a perspective view from the side of an exemplary stock material supply cart for use with a dunnage conversion machine.
Figure 17:
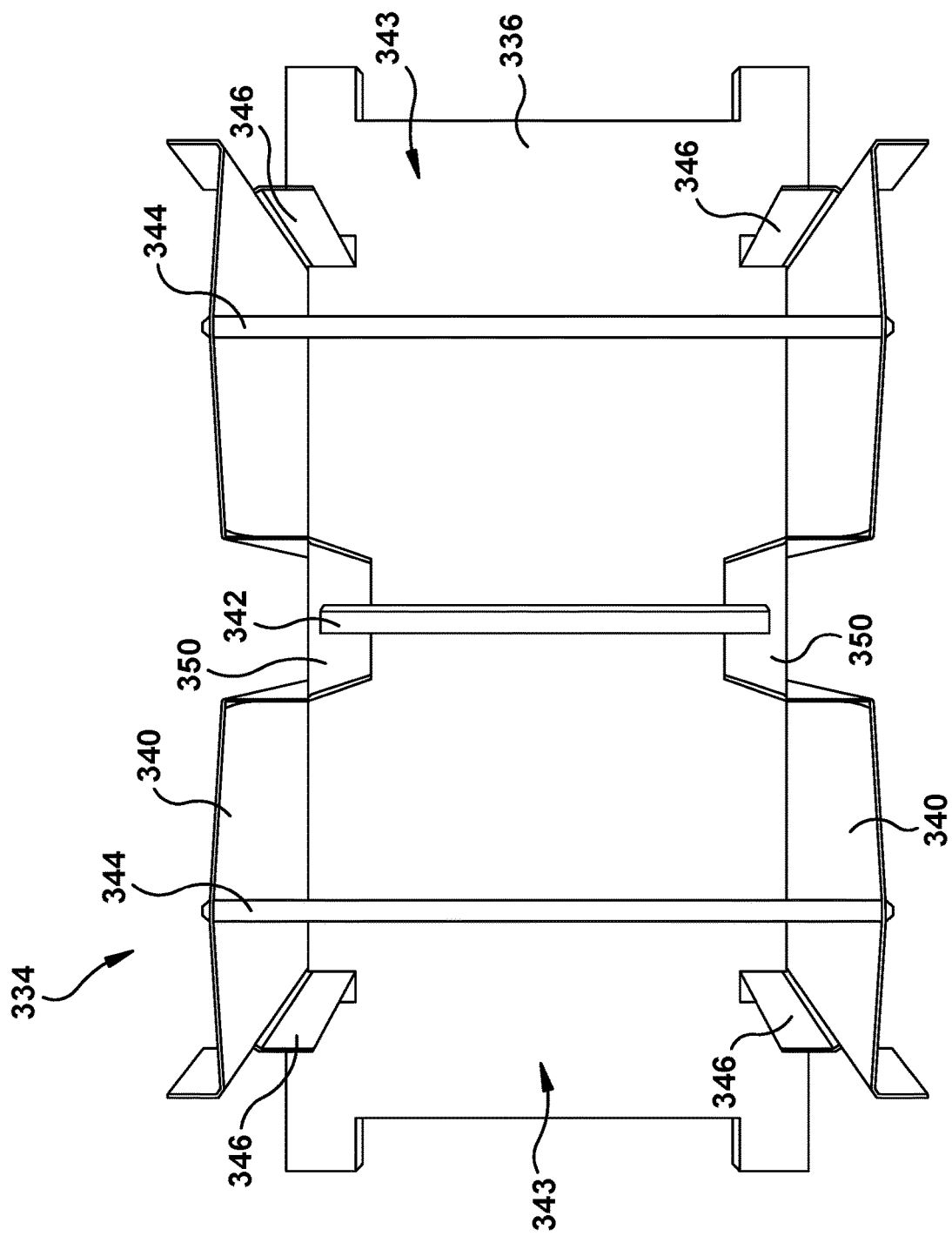
FIG. 17 is a perspective view from above the stock material supply cart of FIG. 16.

An exemplary stock supply assembly 332 in this system 322 supplies two plies $P_1$ and $P_2$ to the dunnage conversion machine 300. To facilitate supplying two plies or webs of sheet stock material to the conversion machine 300, an exemplary stock supply 332 includes a stand 334 (FIGS. 16 and 17) for supporting two separate stacks of fan-fold sheet stock material. An exemplary stand is shown in FIGS. 16 and 17. The stand 334 includes a base 336, a pair of spaced-apart upright frame members 340 having cross-members 342 to hold the upright members 340 upright, and transverse bars or rollers 344 spanning an upper portion of the upright members 340 to help guide the stock material to the conversion machine 300 (FIG. 12). The upright members 340 define opposing substantially-open sides 343 that facilitate loading stacks of fan-fold stock material therein. Lower regions of the open sides 343 include inwardly-extending supports 346 to help support a stack. Additionally, a central portion 350 of the upright members 346 protrudes inwardly to support an opposing side of the stack and separate the two supplies or stacks. These inwardly-extending and inwardly-protruding portions 346 and 350 of the upright members 340 also stiffen the upright frame members 340. Additionally, the illustrated stand 334 is provided with wheels 352 for mobility so that it also functions as a cart.

Figure 13:
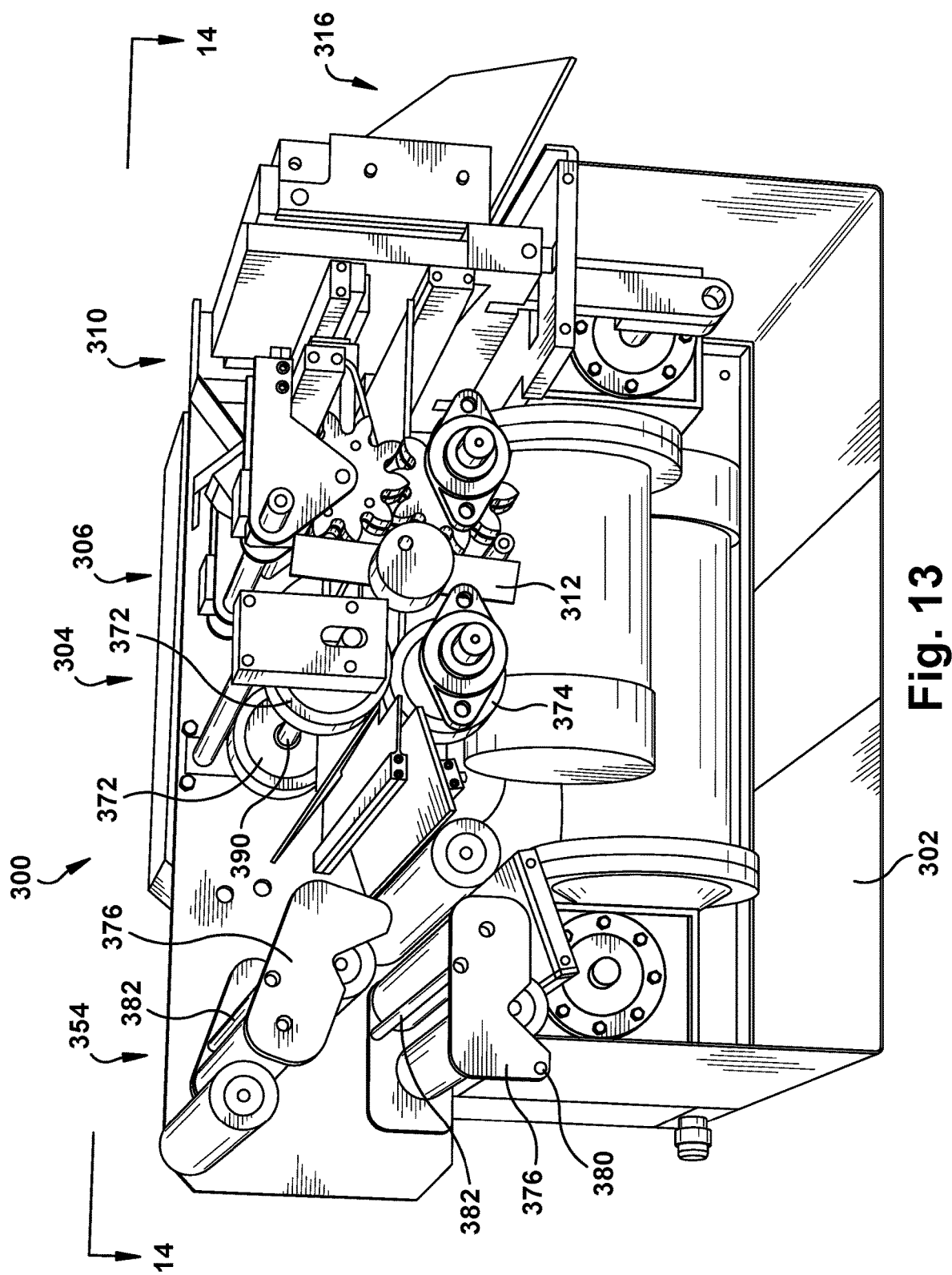
FIG. 13 is a perspective view of the dunnage conversion machine of FIG. 12 with the left side and top panels of its housing removed to reveal the internal components.
Figure 14:
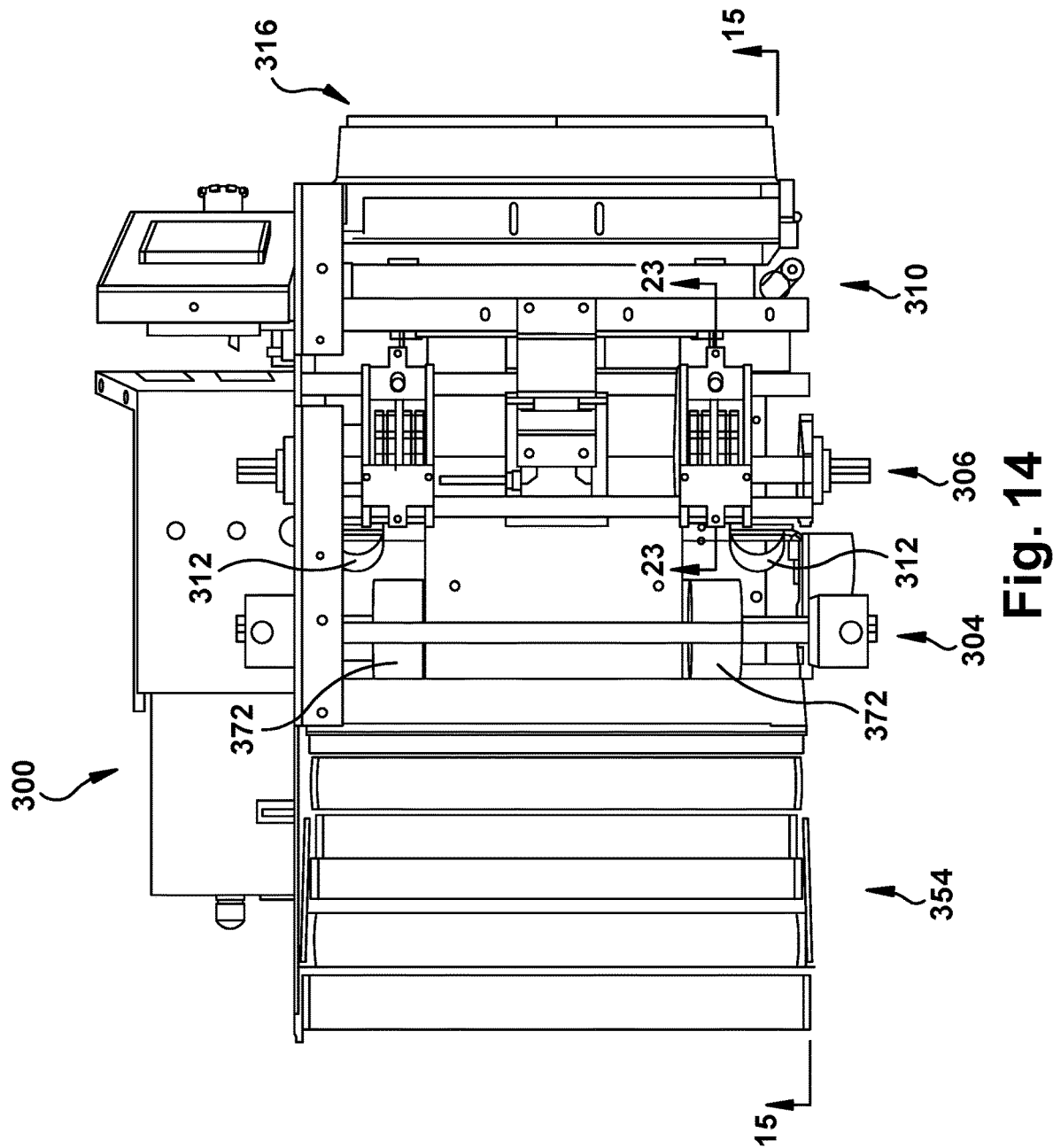
FIG. 14 is a top view of the dunnage conversion machine of FIG. 13, looking in direction 14-14 in FIG. 13.
Figure 15:
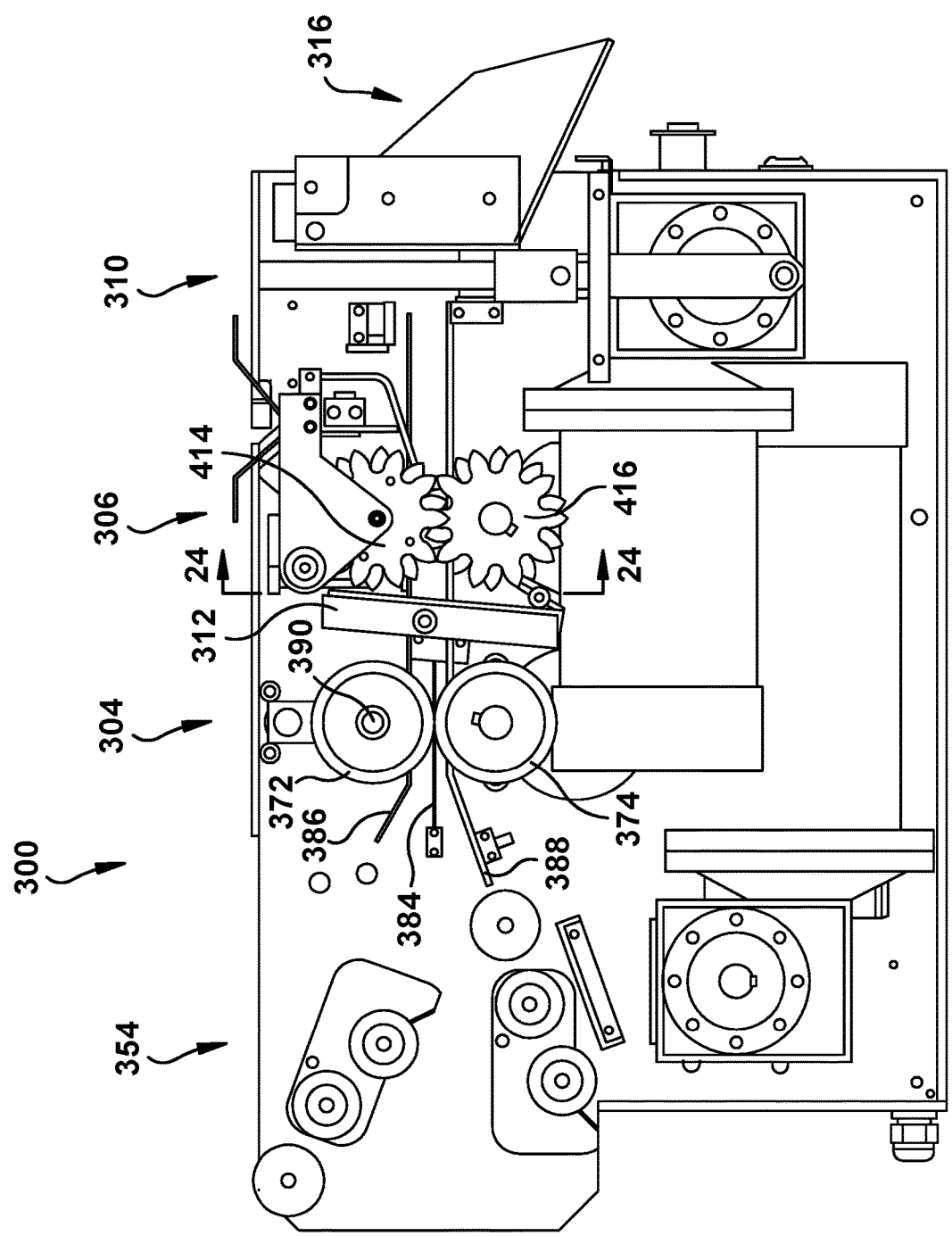
FIG. 15 is a cross-sectional side view of the dunnage conversion machine of FIG. 12, looking in direction 15-15 in FIG. 14.
Figure 18:
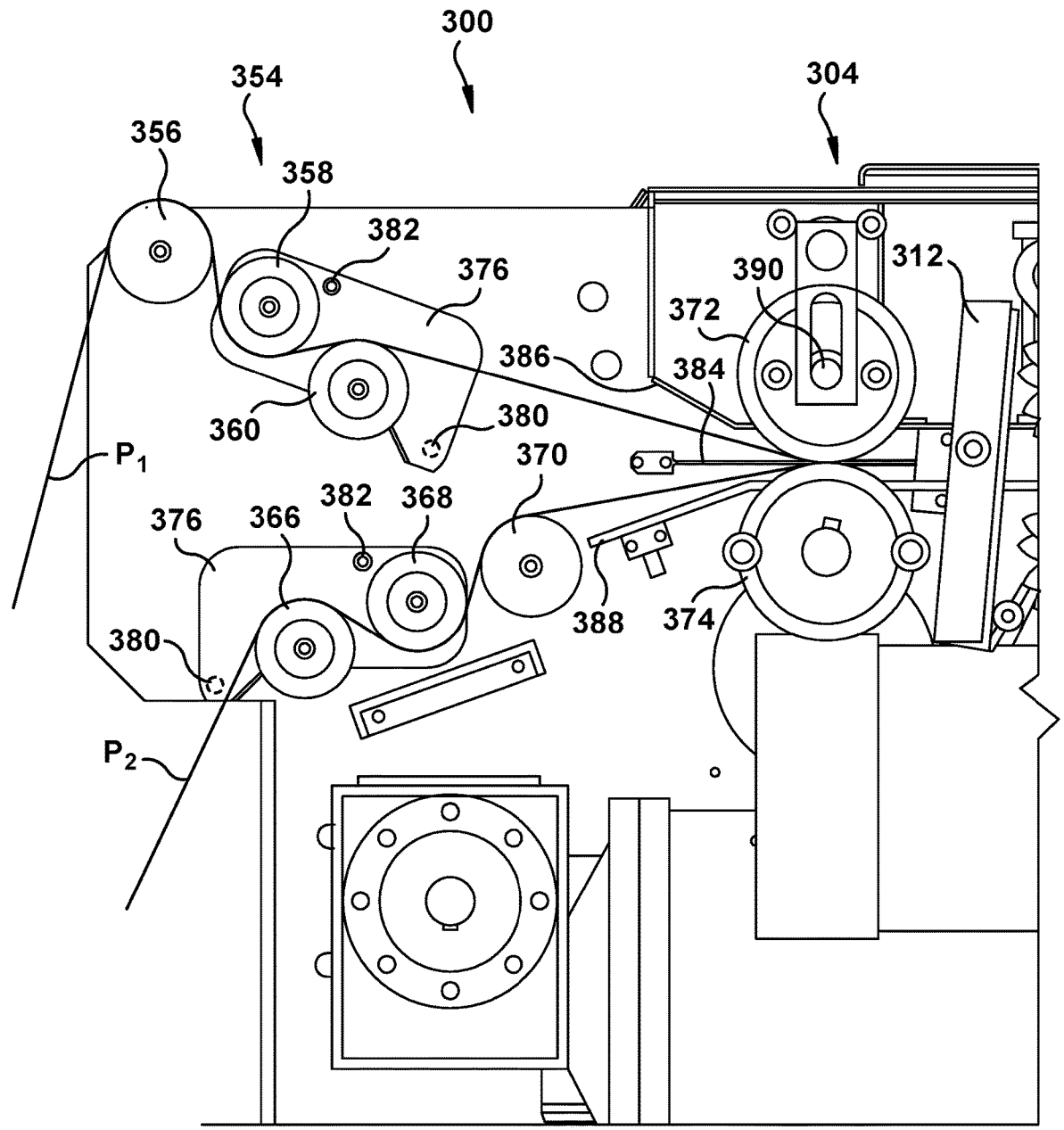
FIG. 18 is an enlarged side view of an upstream end of the dunnage conversion machine of FIG. 15.
Figure 19:
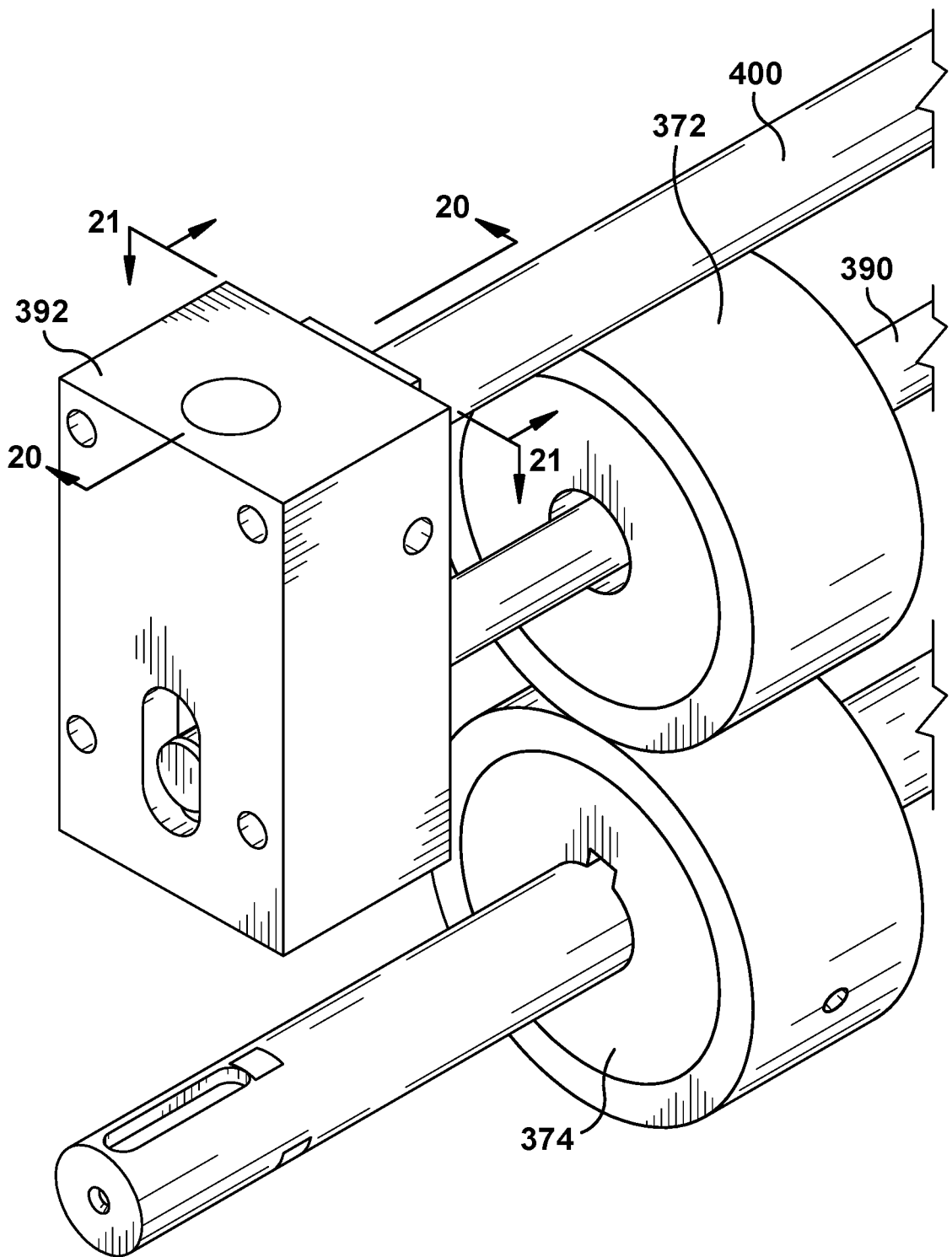
FIG. 19 is an enlarged schematic perspective view of a portion of a feed assembly of the dunnage conversion machine of FIG. 13.
Figure 20:
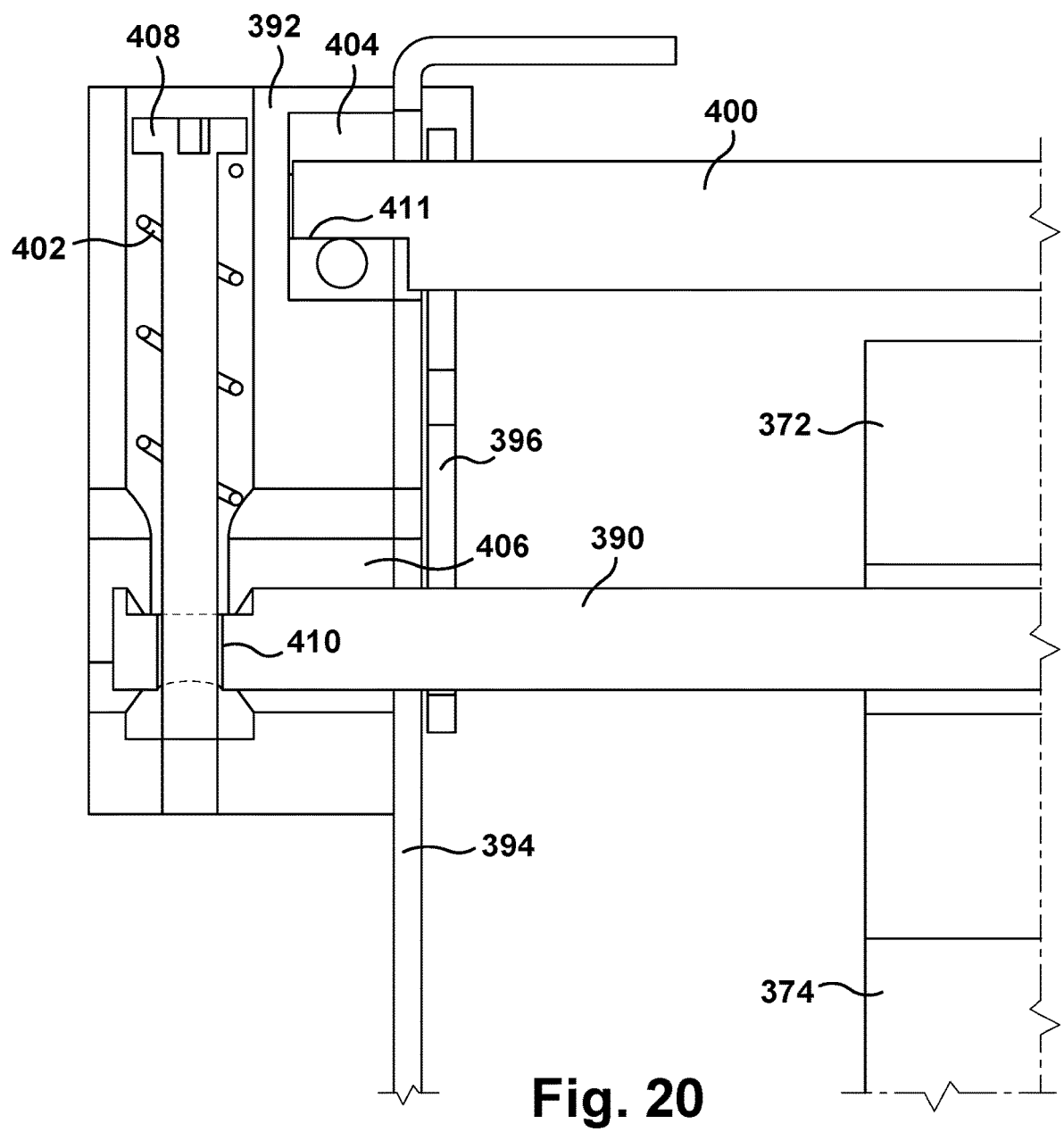
FIG. 20 is a cross-sectional view of FIG. 19 taken along lines 20-20 and looking in the indicated direction represented by the corresponding arrows.
Figure 21:
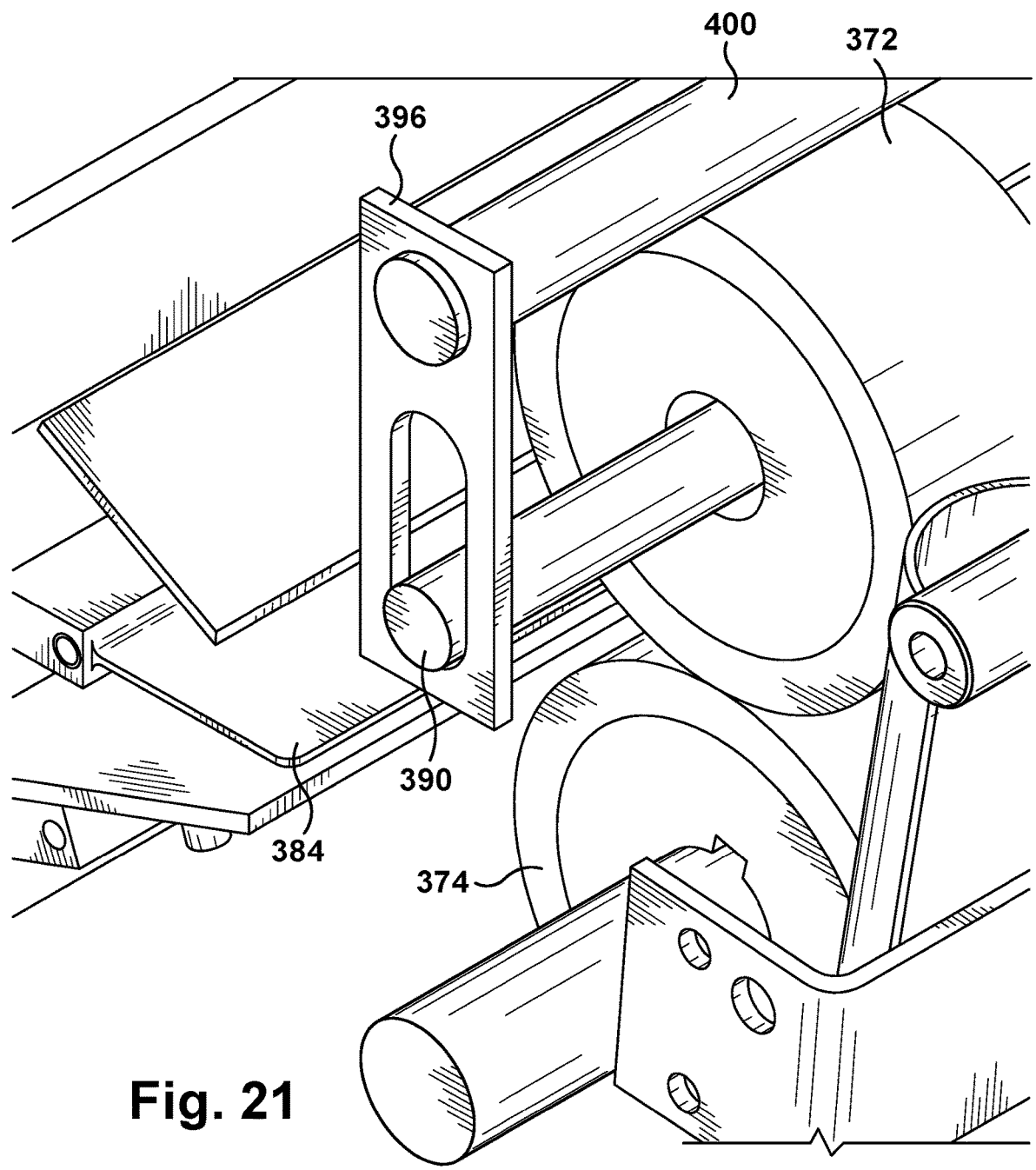
FIG. 21 is a cross-sectional view of FIG. 19 taken along lines 21-21 and looking in the direction indicated by the corresponding arrows.
Figure 22:
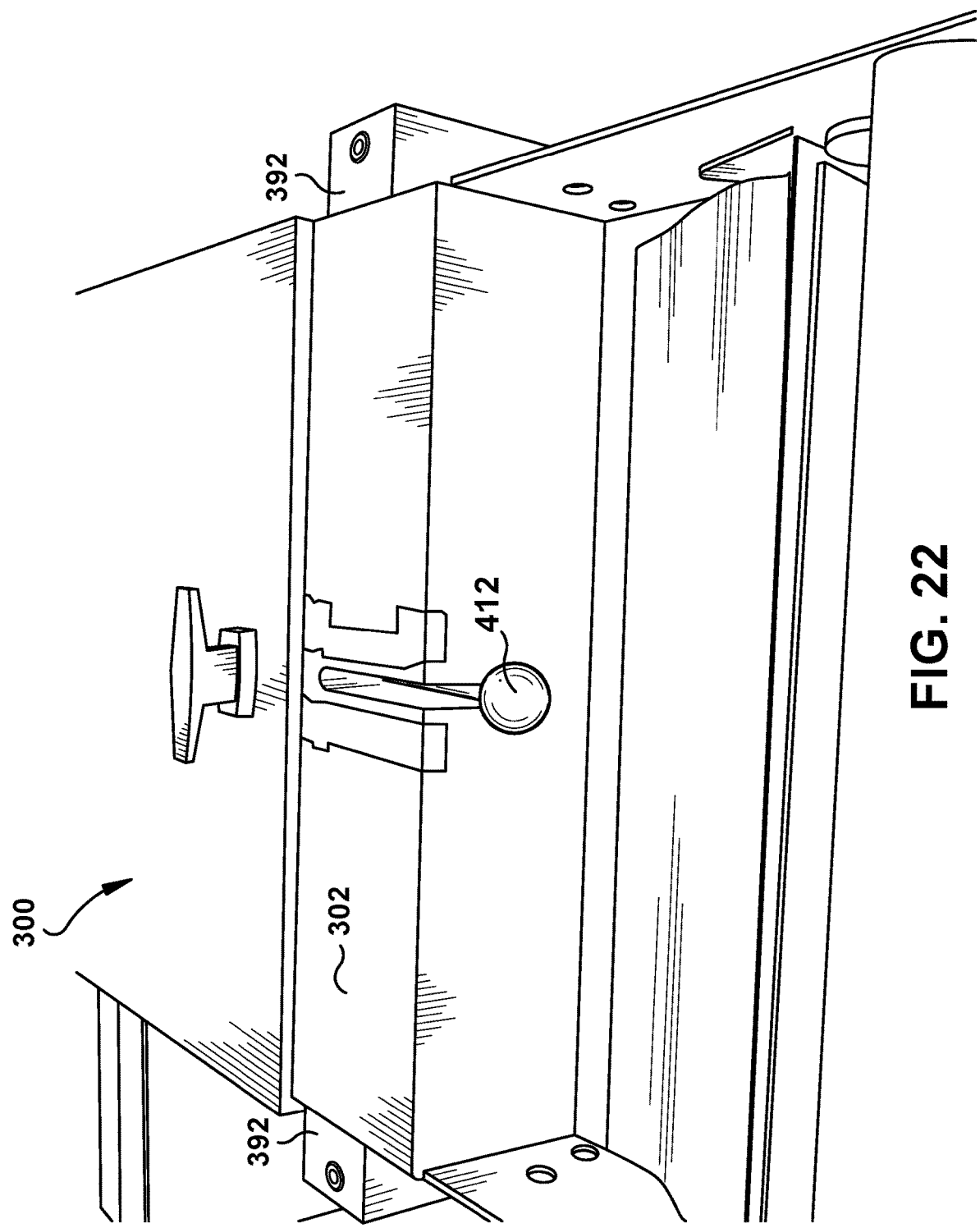
FIG. 22 is a perspective view of a rear, upper portion of the dunnage conversion machine of FIG. 12.

From the stand 334 or other supply 332, each ply $P_1$ and $P_2$ passes through separate sets of serpentine guides 354, shown in FIGS. 13-15 and particularly FIG. 18. The serpentine guides 354 provide both adequate tension and encourage proper tracking of each ply as it enters the feed assembly 304. The serpentine guides 354, mounted at the upstream end of the conversion machine 300, define serpentine paths for each ply of stock material and include an upper set of three rollers 356, 358, and 360 that define a serpentine path for an upper ply of stock material and a lower set of three rollers 366, 368, and 370 that define a serpentine path for a lower ply of stock material. The axes of the rollers in each set generally are provided in respective planes that are angled relative to the downstream direction. As a result, each ply $P_1$ and $P_2$ has a direct path from the outlet adjacent the downstream-most rollers 360 and 370 of each set to upper or lower wheels 372 and 374 of the feed assembly 304.

The center roller 358 and 368 of each set is mounted between a pair of swing arms 376. The swing arms 376 are rotatable about pivots 380 between an operating position in-line with the other rollers 356 and 360 or 366 and 370 and a loading position removed from the operating position. The loading position provides a large passage between the center roller and the other two rollers so that the stock material can be fed between the rollers more easily. Loading then becomes a simple task of laying the stock material over the two rollers and under the center roller and into the feed assembly 304. Then the operator can push the center roller back down to its aligned operating position, thereby weaving the stock material into an undulating or serpentine path through the three aligned rollers. Grab bars 382 and 383 attached to the swing arms 376, parallel to and spaced from the center roller 358 or 368, facilitates manually moving the center roller out of line with the other rollers to the loading position and then back to the operating position in line with the other rollers. The central roller can be secured in the operating position, such as by using a spring-loaded element that engages a detent (not shown).

From the serpentine guides 354, each ply $P_1$ and $P_2$ enters the feed assembly 304 on a respective side of a separator plate 384 that extends between the wheels 372 and 374 of the feed assembly 304 and defines a passage for each ply $P_1$ and $P_2$ between upper and lower channel guides 386 and 388. The channel guides 386 and 388 flare outward, away from one another, at an upstream end to receive the plies, and then extend parallel to each other through the feed assembly 304 and the connecting assembly 306 to guide the stock material therethrough to the cutting assembly 310. As noted previously, the channel guides 386 and 388 also confine the stock material between the feed assembly 304 and the connecting assembly 306.

The feed assembly 332 includes laterally-spaced upper and lower pairs of rotating members or wheels 372 and 374, and a wheel lifter to separate the upper and lower wheels 372 and 374 to facilitate loading a new supply of sheet stock material. Unlike the separately-supported upper wheels 216 (FIG. 10) of the preceding feed assembly, the upper wheels 372 in the feed assembly 304 shown in FIGS. 12-15 are secured to a common shaft 390.

Referring now to FIGS. 19-22, the wheel shaft 390 is supported at its lateral ends by a pair of opposing housing blocks 392 mounted outside the lateral side plate frame members 394, a pair of lifting plates 396 inward of the housing blocks 392, and a lifting cam shaft 400. Each housing block 392 houses a compression spring 402 to bias the upper and lower rotating members or wheels 372 and 374 toward one another. The housing block 392 has a recess or pocket 404 that receives an end of the lifting cam shaft 400 and holds it in place, and through-slots 406 that allows the wheel shaft 390 to translate vertically on parallel guides. The wheel shaft 390 has a hole 410 near its end where a bolt 408 passes through to act as a spring compressor as well as the guide for linear movement of the wheel shaft 390.

The lifting cam shaft 400 is in-line with, parallel to, and above the wheel shaft 390 in the illustrated embodiment. The lifting shaft 400 spans the full width of the feed assembly 304 and its lateral ends are captured within the pockets 404 in the housing blocks 392. One side of each end of the lifting cam shaft 400 is milled down to a flat 411 such that the lifting cam shaft 400 sits below its tangency on the flats 411 in the pockets 404 of the housing blocks 392. The lifting plates 396 have a clearance hole for the cam shaft 400 and a slot for the wheel shaft 390 to allow the translation motion of the wheel shaft therein.

A hole toward the center of the lifting cam shaft 400 receives a lever arm 412 that can extend outside the housing 302 of the conversion machine 300. The hole and the lever arm 412 are parallel to the flats 411 in the illustrated embodiment. Rotating the lever arm 412 through ninety degrees from an operating position to a loading position rotates the ends of the cam shaft 400 off their flats 411 onto their round portions. The lifting plates 396 transfer this rotational motion to the wheel shaft 390, and thus to the upper rotating members or wheels 372, thereby providing a gap between the upper and lower wheels 372 and 374, between which the sheet stock material can be fed without obstruction all the way to rotating gears 414 and 416 in the connecting assembly 306 (FIG. 15). Once the stock material is loaded, returning the lever arm 412 to its operating position closes the gap between the upper and lower wheels 372 and 374 of the feed assembly 304. In the operating position, the spring 402 biases the shaft 390 of the upper wheels 372 toward against the lower wheels 374, now with the stock material therebetween.

As mentioned above, the conversion machine 300 includes forming plows 312 shown in FIGS. 13-15 of essentially the same shape as in the previous embodiment, mounted between the feed assembly 304 and the connecting assembly 306 to urge inwardly lateral edge portions of the sheet stock material. The lateral edge portions of one ply also may turn or fold over the edge portions of another ply, and the resulting increased number of layers will be connected together as they pass between the gears 414 and 416 of the connecting assembly 306.

Figure 23:
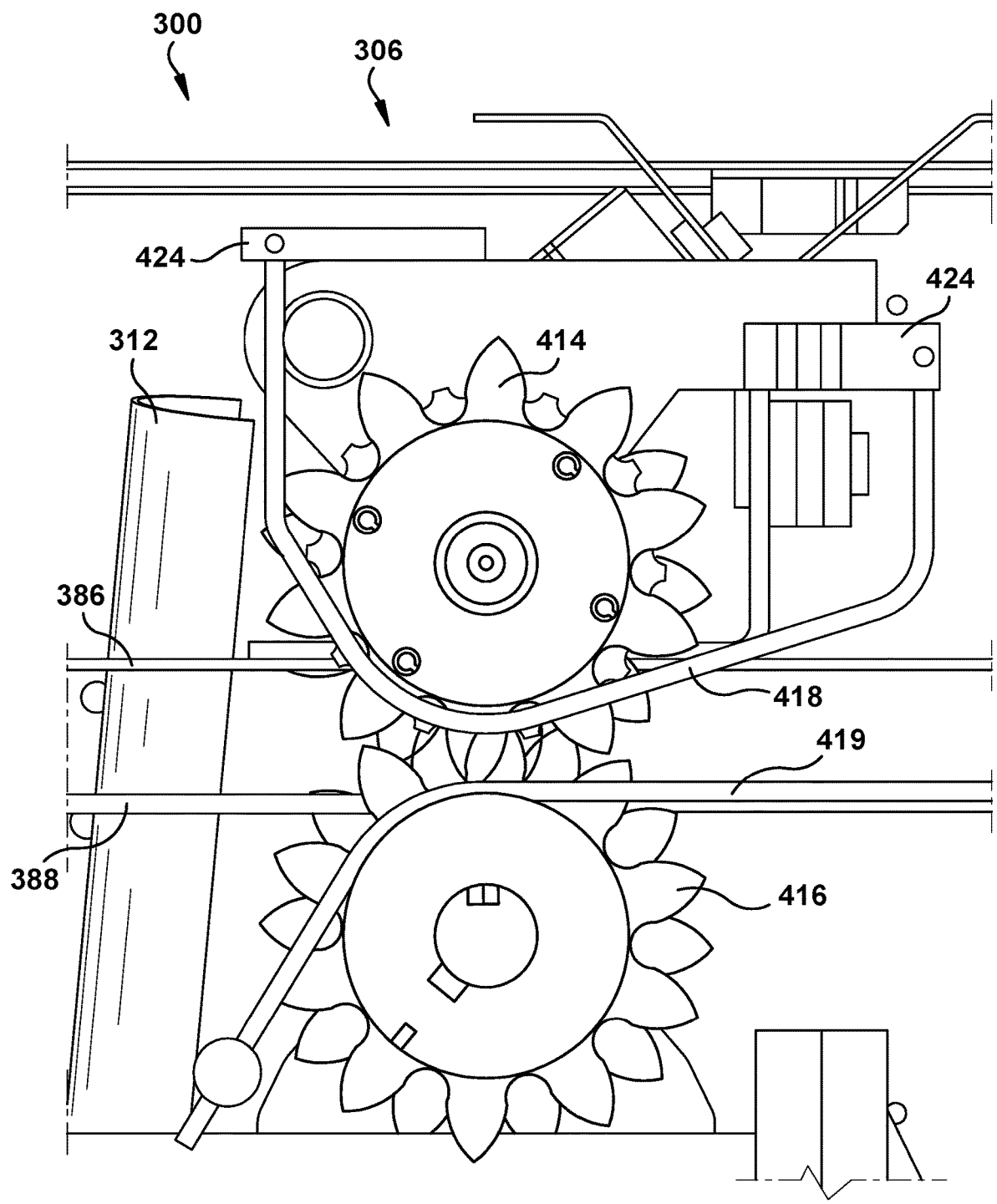
FIG. 23 is an enlarged cross-sectional view of a portion of a connecting assembly of the dunnage conversion machine of FIG. 13 looking in direction 23-23 of FIG. 14.
Figure 24:
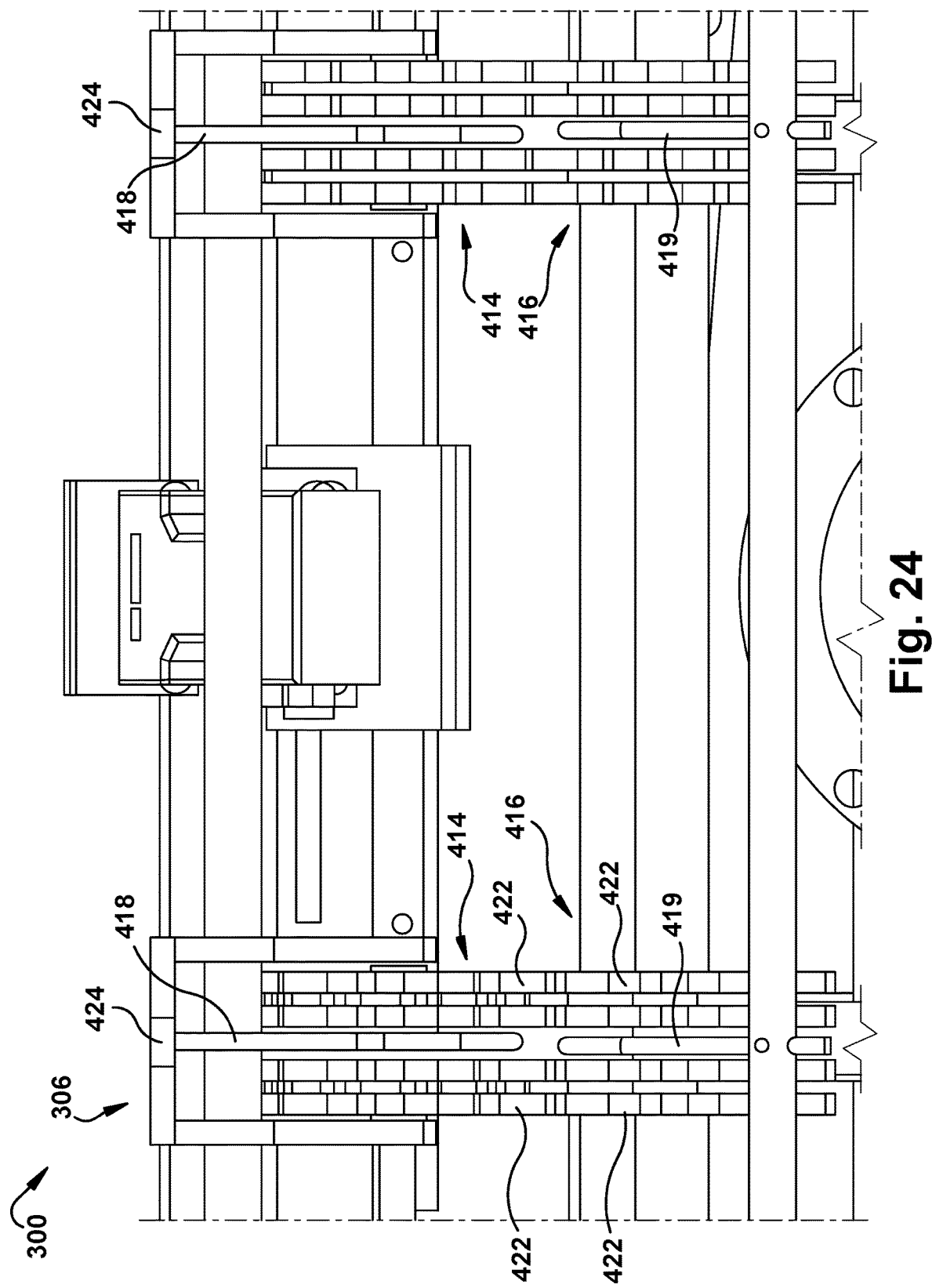
FIG. 24 is an enlarged cross-sectional view of a portion of the connecting assembly of the dunnage conversion machine of FIG. 13, looking in direction 24-24 of FIG. 15.

Referring now to FIGS. 23 and 24, to assist the channel guide plates 386 and 388 in guiding the crumpled stock material past the gears 414 and 416 in the connecting assembly 306, the conversion machine 300 employs stripper bars 418 and 419 to strip crimped stock material from between the teeth of the gears 414 and 416 to minimize or prevent jamming of the stock material in the gears 414 and 416. Each stripper bar 418 and 419 extends through an annular recess or valley between laterally-spaced gear segments 422. Because the stripper bars 418 and 419 are smaller than the space between the gear shafts 421 and 423 and the diameter of the gears 414 and 416 between the gear teeth, and passes the gear at a point adjacent the shaft, they do not interfere with the connecting operation in any way. The upper strippers 418 on the biased idler gears 414 are attached to a gear support 424 upstream and downstream of each gear 414, allowing the stripper bars 418 to move with the pivotable gear support 424 while still providing the necessary stripping action in a central portion of the gear 414. The lower stripper member 419 is fixed and does not move, since the lower gear 416 only rotates.

Figure 25:
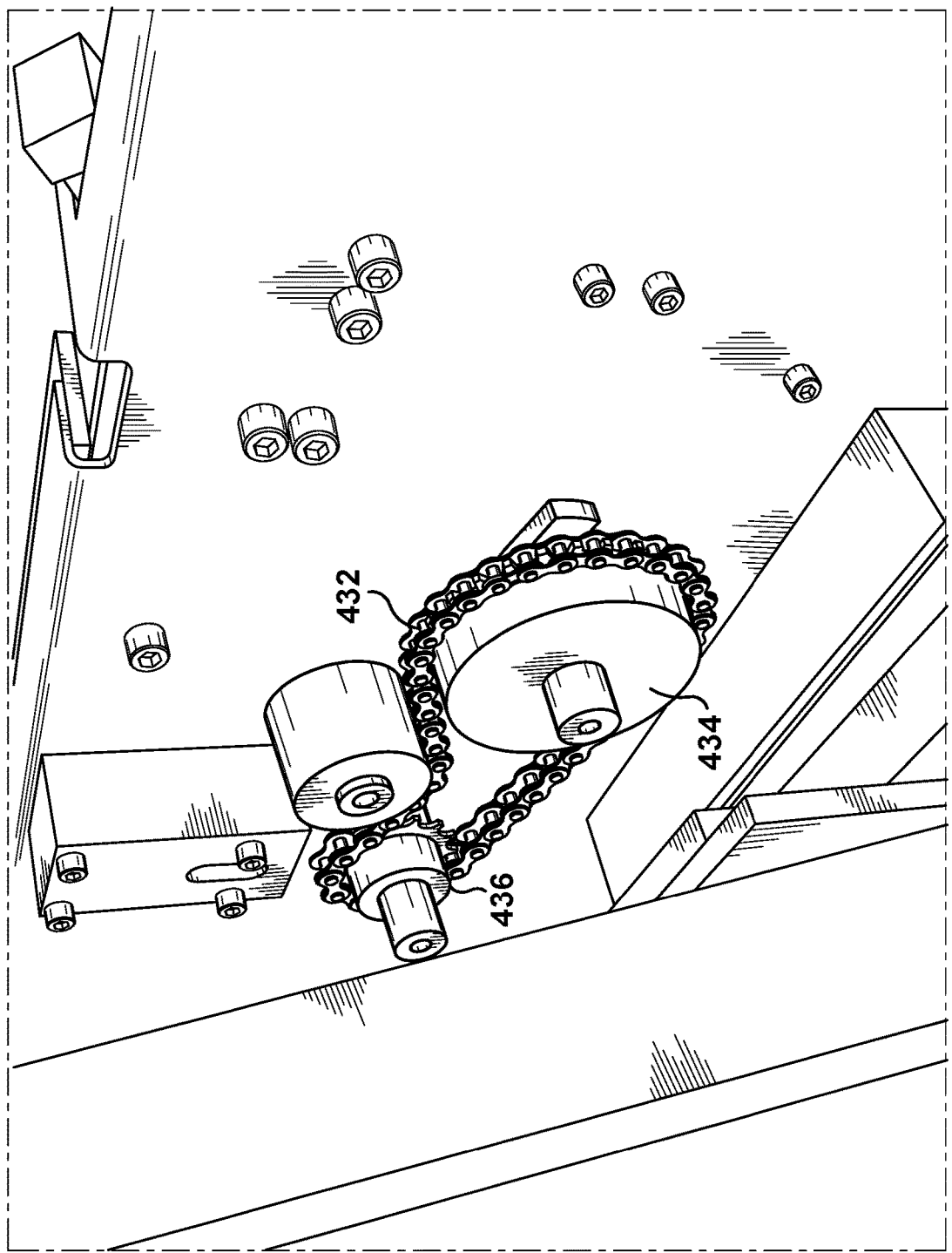
FIG. 25 is a perspective view of a drive chain portion seen from the right of the dunnage conversion machine of FIG. 13 with the relevant covers of the housing removed to reveal its components.

As in the previous embodiment, the feed assembly 304 and the connecting assembly 306 are driven by a common drive motor 430. The drive motor 430 is connected to the lower wheels 374 of the feed assembly 304 and the lower gears 416 of the connecting assembly 306 via a drive chain 432 and respective sprockets 434 and 436, as seen in FIG. 25. Since the drive sprockets 434 and 436 that are used to drive the wheels 372 and 374 of the feed assembly 304 and the gears 414 and 416 of the connecting assembly 306 are located outside the side plate frame members or walls 394, the sprockets 434 and 436 are readily accessible. Changing the chain 432 and a sprocket 434 and 436 are the only items necessary to change the amount of crimp loss and average crumpling frequency. While this approach is relatively simple and inexpensive, the machine can alternatively include a transmission and/or separate motors to control the relative speeds on the fly, without stopping the conversion process. As noted above, the relative amplitude of the crumpling generally is defined by the separator plate 384 and its distance from the upper and lower guide plates 386 and 388 (FIG. 15).

Figure 26:
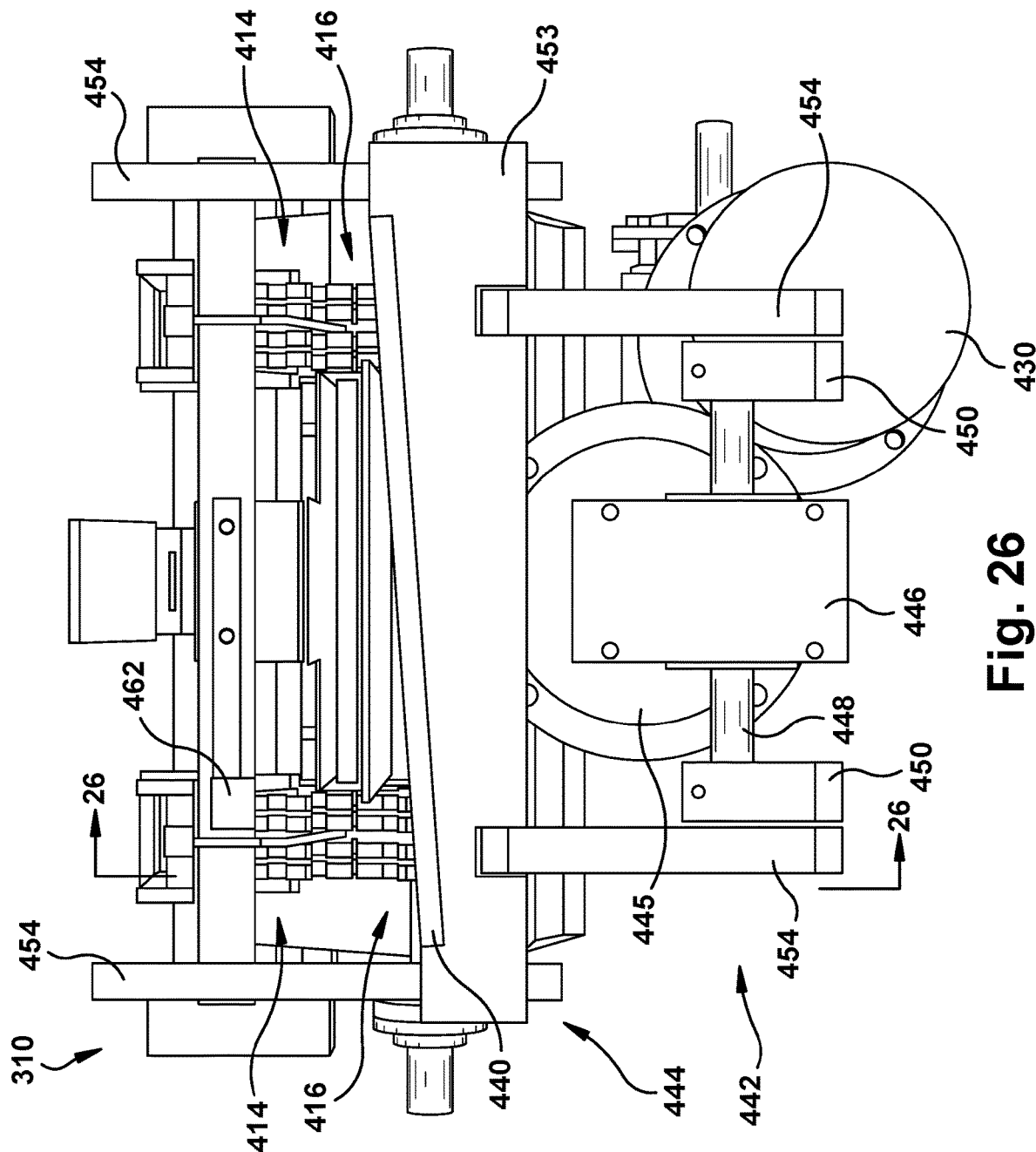
FIG. 26 is a front elevation view of a downstream portion of the dunnage conversion machine of FIG. 12 with the housing removed to reveal a cutting assembly.
Figure 27:
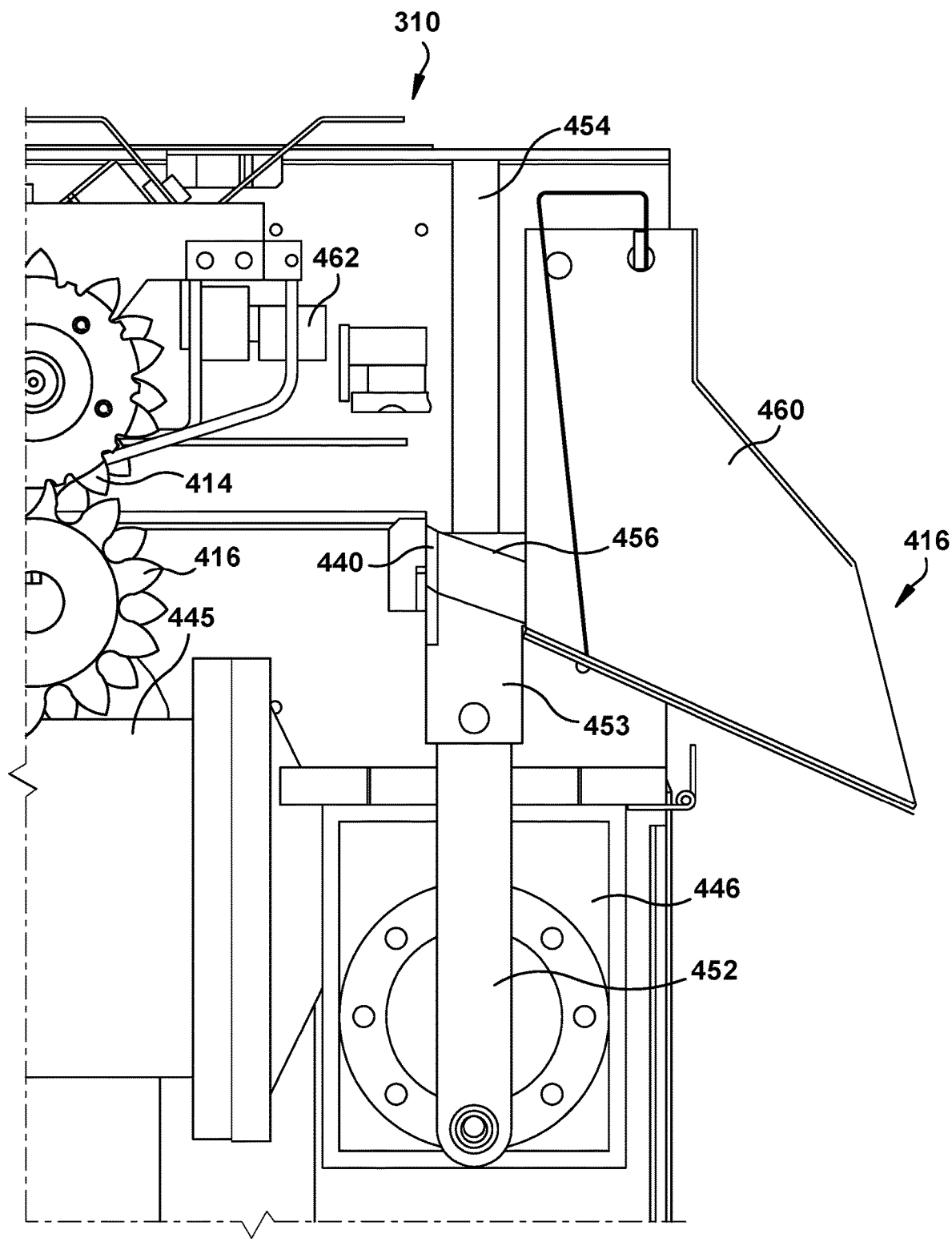
FIG. 27 is an enlarged cross-sectional view of the cutting assembly of FIG. 26 as seen along lines 26-26.

The connected strip of dunnage exiting the connecting assembly 306 passes downstream to the cutting assembly 310. The cutting assembly 310 in this embodiment is shown in FIGS. 26 and 27 and is similar to the cutting assembly 208 (FIG. 9) in the previous embodiment. The cutting assembly 310 includes a guillotine-style cutting blade 440 whose movement is directed by a twin four-bar linkage 442 and a slider assembly 444. A separate cut motor 445 drives the four-bar linkage 442 via a gear box 446. A drive shaft 448 symmetric about the gear box 446 has a drive crank 450 on opposing ends of the shaft 448. Each drive crank 450 is attached to a second crank 452 which in turn attaches to a carriage 453 that supports the cutting blade 440. The cutting blade carriage 453 rides on a pair of parallel shafts or slider arms 454 to guide the cutting blade 440 as it moves across the path of the strip of dunnage to sever a discrete length of a wrapping dunnage product from the strip. Each of the crank arms 450 is aligned with one of the laterally-spaced gear pairs 414 and 416 of the connecting assembly 306 to concentrate the force applied to cutting the strip of dunnage at the connecting lines, which are the areas of maximum resistance to being cut.

The cutting blade carriage 453 has an angled surface 456 behind the blade edge. This angle removes any flat surface upon which slivers of the cut dunnage product could rest. From the cutting blade 440, the housing exit chute 460 continues a downward slope out of the machine 300. This allows the next strip of dunnage formed in series to sweep out the remnants from the previous strip of dunnage.

Finally, this conversion machine 300 also provides two ways to detect jams. Refer back to FIGS. 12-15. First, the controller 330 senses when the speed of the drive motor 430 falls below a set limit compared to its intended running speed. Second, an optical sensor 462 is mounted near the idler gear support 424 in the connecting assembly 306. This sensor 462 has a fixed focal length, and when the stock material backs-up, narrowing the gap between the sensor and the original path of the stock material, the controller 330 identifies this as a jam and the controller 330 can stop the machine 300 and output a signal to alert an operator.

These features of the dunnage conversion machine 300 make it easier to load, improve the tension and tracking of the incoming plies of stock material as well as the cutting of a dunnage product from the strip, and allow the conversion machine to operate longer without jamming, yet quickly alert an operator in the event of a jam. All while still producing a quality wrapping dunnage product in a compact machine on-demand in the desired length as needed.

In summary, and referring to FIG. 1, the present invention provides a dunnage conversion machine 36 converts a sheet stock material into a dunnage product that is relatively thicker and less dense than the stock material, but is relatively thin and sufficiently flexible to function as a protective wrap. The conversion machine 36 includes a feed mechanism 40 that advances a sheet stock material therethrough and a connecting mechanism 42 downstream of the feed mechanism 40. The connecting mechanism 42 retards the passage of the sheet stock material therethrough by feeding the stock material therethrough at a slower rate than the feed mechanism 40 feeds the stock material to the connecting mechanism 42. This causes the stock material to randomly crumple in a longitudinal space between the feed mechanism 40 and the connecting mechanism 42. The connecting mechanism 42 connects multiple overlapping layers of sheet stock material together as they pass therethrough, including connecting at least one crumpled sheet to one side of one other sheet.

Sliding Stock Supply Shelf

The present invention also provides a dunnage conversion machine having a shelf for supporting a supply of stock material, a conversion assembly for converting stock material into a dunnage product dispensed through an outlet in a downstream direction, and a stand that supports the conversion assembly and the shelf. The shelf is linearly movable between an operating position adjacent the conversion assembly and a loading position spaced from the operating position for loading stock material without moving the conversion assembly.

Figure 28:
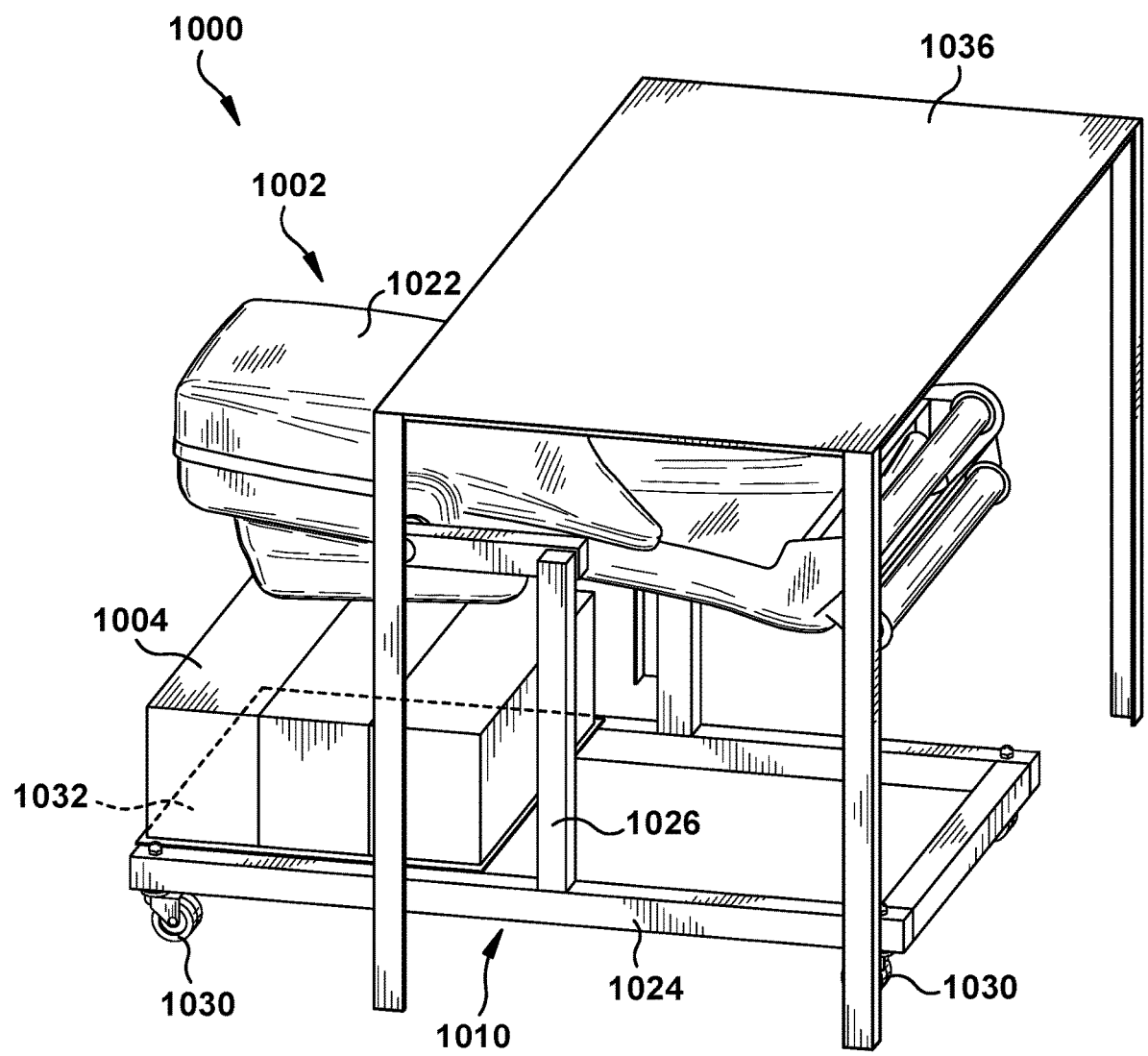
FIG. 28 is perspective view of an exemplary dunnage conversion machine with a sliding shelf in accordance with the present invention.
Figure 31:
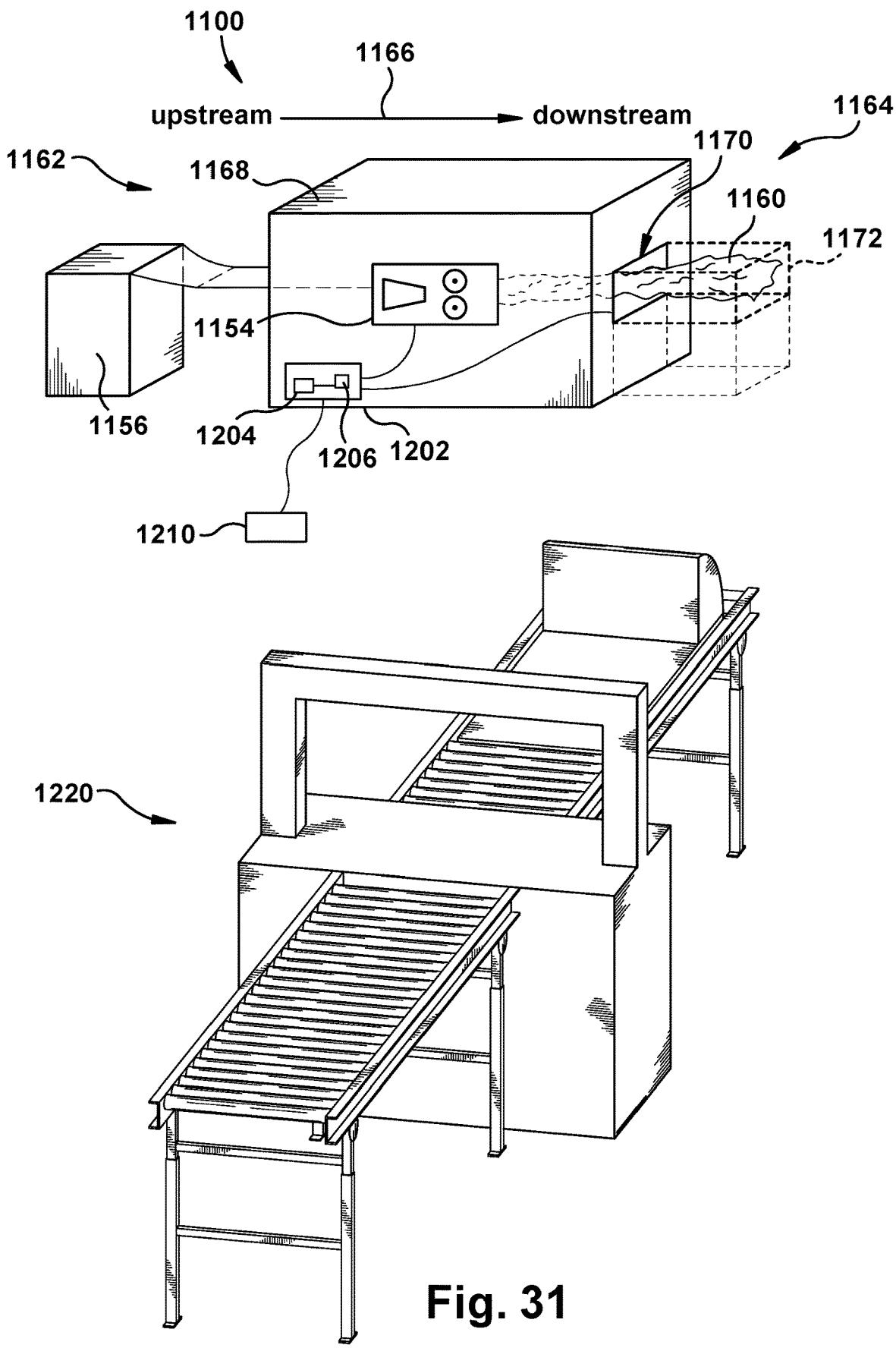
FIG. 31 is a schematic perspective view of another dunnage conversion machine provided in accordance with the present invention.
Figure 32:
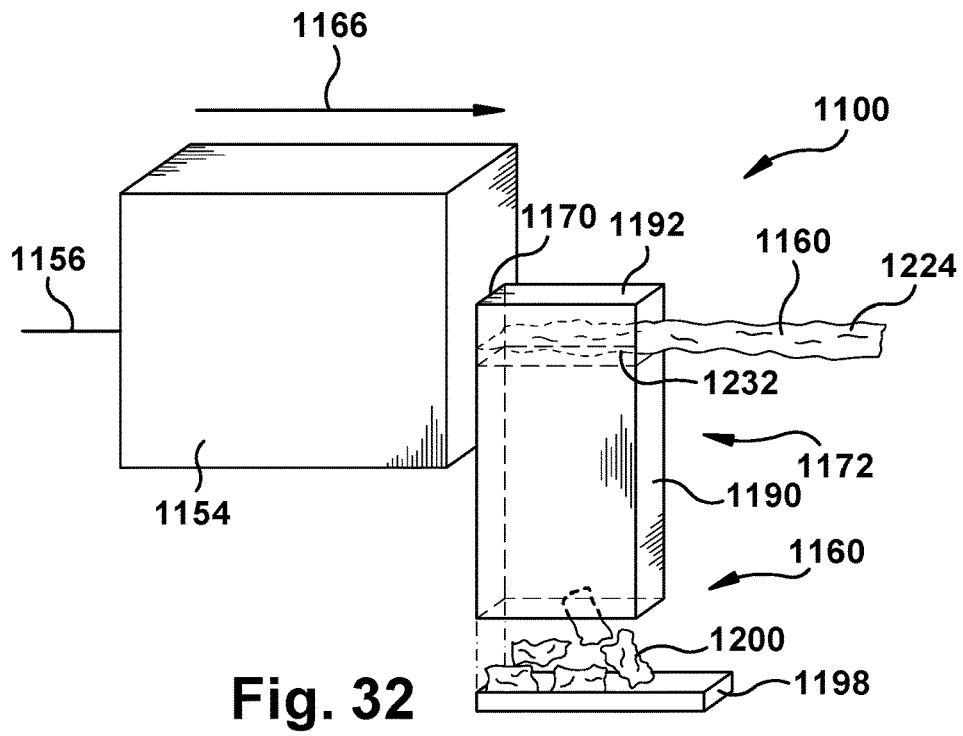
FIG. 32 is a schematic illustration of the dunnage conversion machine of FIG. 31 with an exemplary output chute provided in accordance with the present invention.

Referring now in detail to the drawings and initially to FIGS. 28-30, the present invention provides a dunnage conversion machine 1000 for producing dunnage products for use in packing objects in a container. The conversion machine or converter 1000 includes a dunnage conversion assembly 1002 for converting a stock material 1004 into a dunnage product 1006 and a stand 1010 that supports the conversion assembly 1002.

The conversion assembly 1002 is capable of converting the stock material 1004 into a dunnage product 1006 as the stock material moves through the conversion assembly in an upstream-to-downstream direction, from an upstream end 1014 to a downstream end 1016. The converter 1000 typically includes a housing 1022 for the conversion assembly 1002. The conversion assembly 1002 dispenses the dunnage product 1012 through an outlet 1020 defined by a downstream end of the housing 1022. Any type of conversion assembly that converts a stock material into a relatively less dense dunnage product can be used in accordance with the present invention. An exemplary conversion assembly is disclosed in U.S. Pat. No. 6,676,589, which is hereby incorporated by reference.

The stand 1010 includes a frame 1024 with uprights 1026 for supporting the conversion assembly 1002 at an elevated position, and can also include one or more wheels 1030 to help transport the converter 1000.

In addition to the conversion assembly 1002, the stand 1010 also supports a shelf 1032 for supporting a supply of stock material 1004. The shelf 1032 defines a horizontal, substantially flat and continuous surface for supporting the supply of stock material.

The stock material 1004, such as a container of stock material or a stack of fan-folded sheet stock material is supported on the shelf 1032 to be fed into the conversion assembly 1002 for conversion into a dunnage product 1006. An exemplary stock material 1004 includes one or more stacks of fan-folded kraft paper. The stock material 1004 supported on the shelf 1032 can be fed into the upstream end 1014 of the conversion assembly 1002 for conversion into dunnage products 1006.

The shelf 1032 is linearly movable between a working or operating position (FIG. 29) adjacent the conversion assembly 1002 and a loading position (FIG. 30) spaced from the operating position for loading stock material without moving the conversion assembly 1002. The illustrated stand 1010 supports the conversion assembly 1002 above the shelf 1032. In the operating position, the shelf 1032 is under the conversion assembly 1002.

In the illustrated converter 1000, the shelf 1032 is mounted to the stand 1010 by a pair of parallel, spaced apart, telescoping support and guide members 1034, such as commonly available drawer slides. Both the outlet 1020 of the conversion assembly 1002 and shelf 1032 in the loading position are on the same side of the conversion machine 1000. The packer or other operator both can retrieve dunnage products 1006 from the outlet 1020 and load the stock material 1004 from the downstream end 1016 of the converter 1000. This is advantageous when space is limited, such as when the conversion assembly 1002 is positioned underneath a table 1036 or other work surface as shown in FIG. 28. This allows an operator to more efficiently supply stock material, splice a new supply of stock material to an almost-spent supply stock material, and/or return to a packing operation as quickly as possible.

An exemplary method of loading a dunnage conversion machine 100 thus includes the following steps: (a) linearly moving the shelf 1032 from the operating position (FIG. 29) to the loading position (FIG. 30) without moving the conversion assembly 1002, (b) loading a supply of stock material 1004 onto the shelf 1032, and (c) returning the shelf 1032 to the operating position (FIG. 29). The method can also include the step of splicing a new supply of stock material to an almost-spent supply of stock material before the step of (c) returning the shelf 1032 to the operating position.

Short-Dunnage Output Chute Bypass

In the place of or in addition to the shelf, the conversion machine can include an output chute with an upstream end that is moveable relative to the outlet. In a first position, the output chute is aligned with the outlet to receive dunnage products, and in a second position the upstream end of the output chute is moved out of alignment with the outlet so that dunnage products from the conversion assembly bypass the output chute.

To dispense dunnage products with lengths both under and over a minimum length to prevent jamming in a typical output chute, the present invention provides an output chute that can be moved out of the way to dispense relatively short dunnage products along a separate path that does not go through the output chute.

Turning now to FIGS. 31-38 an exemplary dunnage conversion machine or converter 1100 is shown. The converter 1100 includes a conversion assembly 1154 that converts a stock material 1156 into a dunnage product 1160 as the stock material travels from an upstream end 1162 of the conversion assembly 1154 to a downstream end 1164 in an upstream-to-downstream direction 1166. Any conversion assembly that is capable of producing dunnage products of multiple lengths can be used in the converter 1100 provided by the invention.

The converter 1100 includes a housing 1168 for a conversion assembly 1154. A downstream end of the housing 1168 defines an outlet 1170 for the conversion assembly 1154. The conversion assembly 1154 dispenses dunnage products 1160 through the outlet 1170 in a downstream direction 1166. The distance between the downstream end of the conversion assembly 1154 and the outlet 1170 is less than a predetermined minimum dunnage product length. In an exemplary embodiment, the outlet 1170 defined by the housing 1168 is less than five centimeters downstream of a downstream end of the conversion assembly 1154.

The converter 1100 also includes a chute 1172 adjacent the outlet 1170. The chute 1172 has a gravity chute portion 1190 that extends in a direction transverse the downstream direction 1166, and an output chute portion 1192, also referred to more simply as the output chute. The output chute portion 1192 is movable between a first position (FIG. 32) where an upstream end of the output chute portion 1192 is aligned with the outlet 1170, and a second position (FIG. 33) where the upstream end of the output chute 1192 is spaced from the outlet 1170 and its first position so that dunnage products exiting the outlet 1170 bypass the output chute portion 1192. The conversion assembly 1154 is operative whether the output chute 1192 is in either the first position or the second position.

Figure 33:
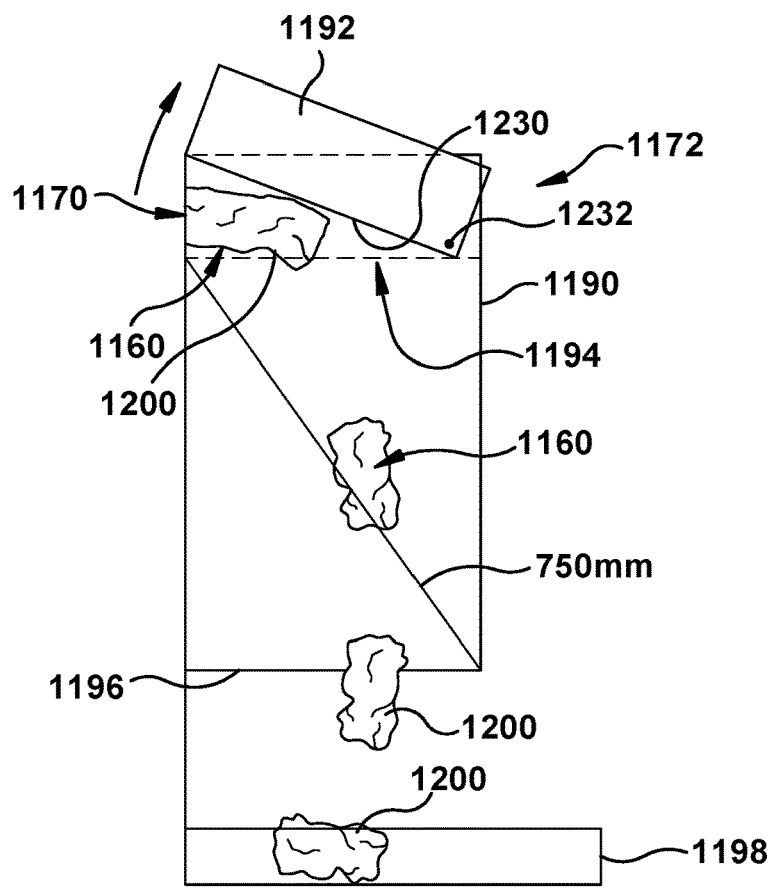
FIG. 33 is an enlarged cross-sectional elevation view of the output chute of FIG. 32.
Figure 34:
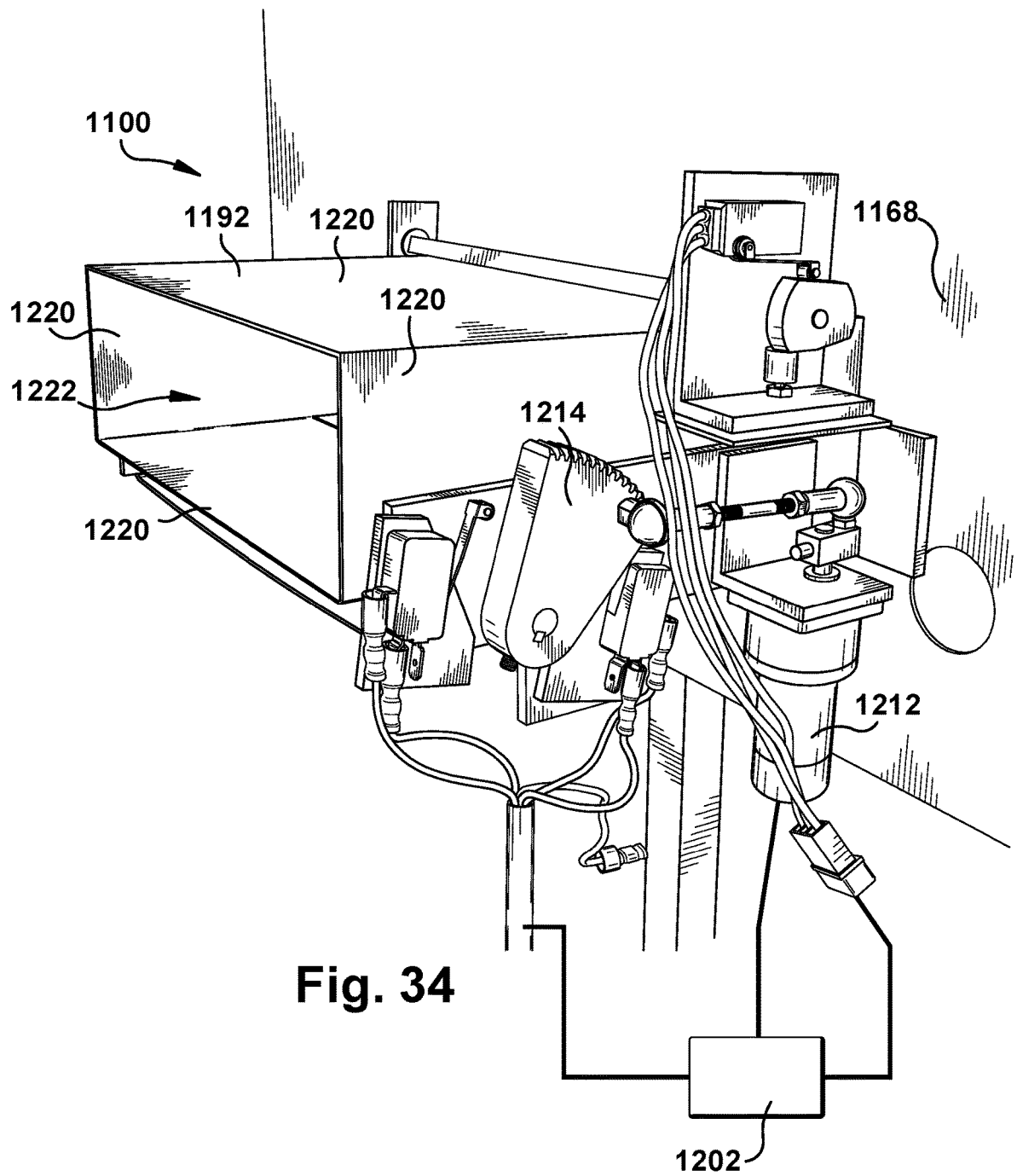
FIG. 34 is a perspective view of another exemplary output chute provided in accordance with the present invention, with the output chute in a first position.
Figure 35:
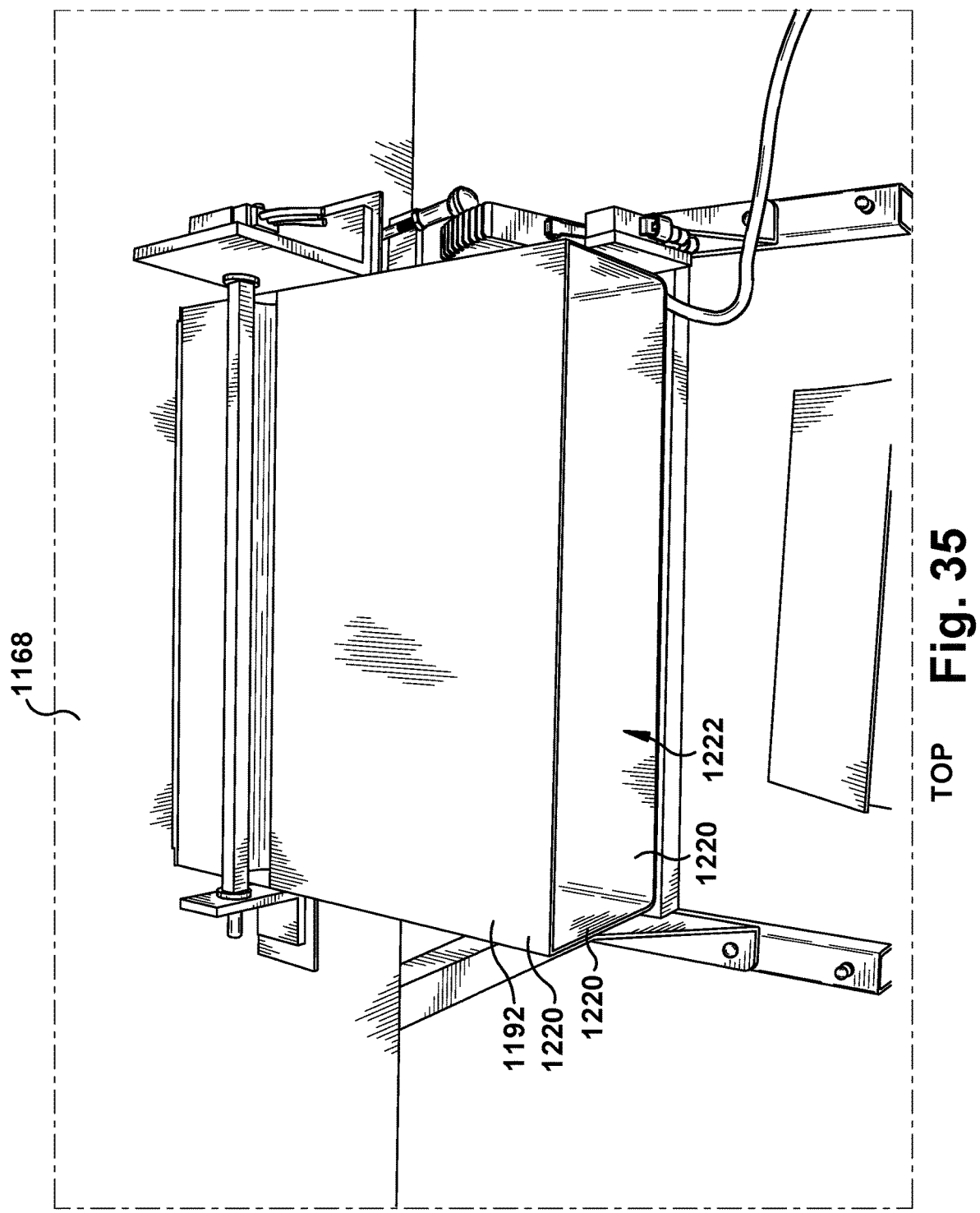
FIG. 35 is a top view of the output chute of FIG. 34.
Figure 36:
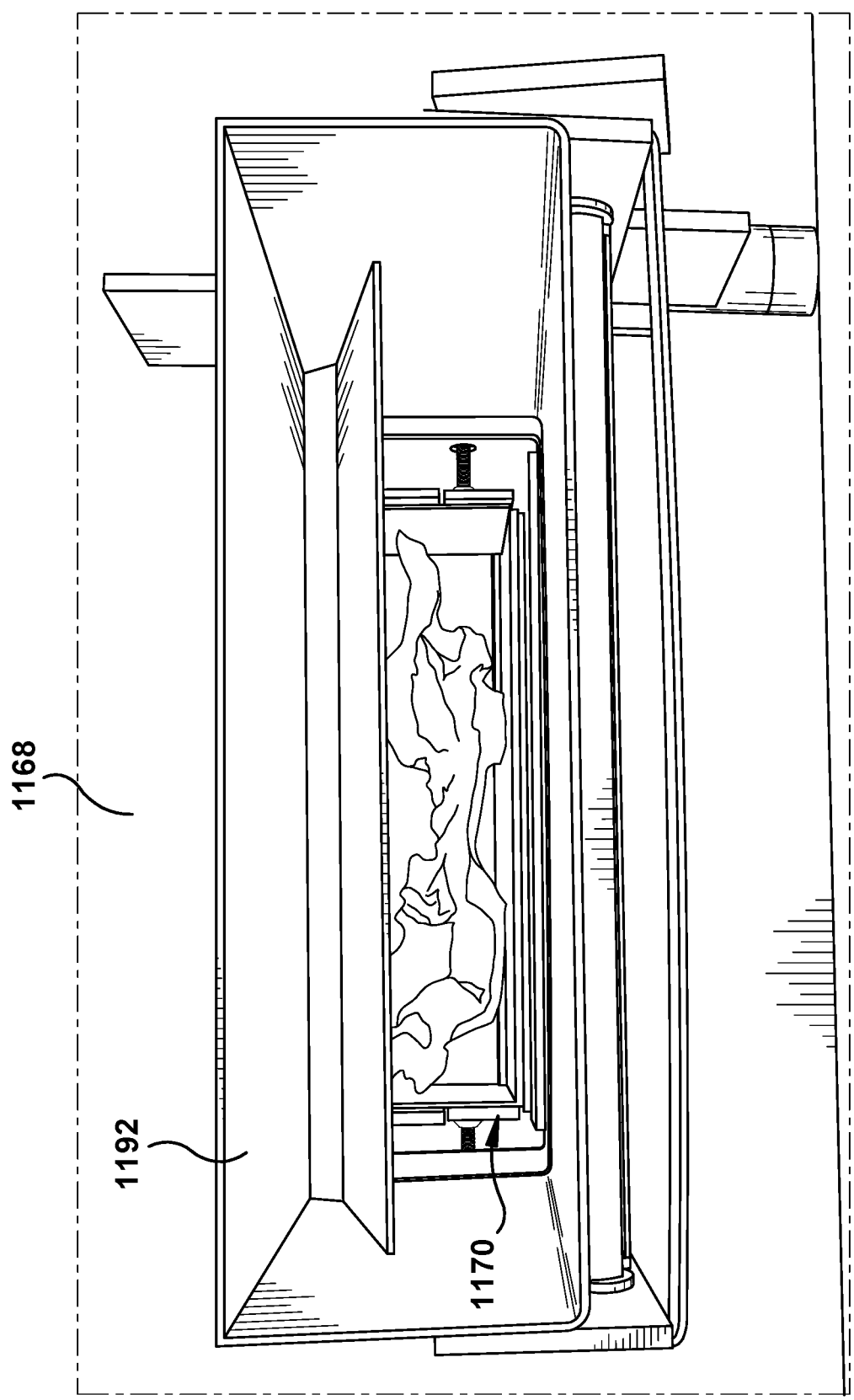
FIG. 36 is an end view of the output chute of FIG. 34.

The gravity chute portion 1190 has an entrance 1194 adjacent the outlet 1170. The output chute portion 1192 closes the entrance 1194 to the gravity chute 1190 when the output chute portion 1192 is in the first position (FIG. 32) and opens the entrance 1194 to allow dunnage products 1160 to enter the gravity chute portion 1190 when the output chute portion 1192 is in the second position (FIG. 33). The gravity chute 1190 has an exit 1196 for retrieving dunnage products that is at least 750 millimeters from the conversion assembly outlet 1170. In the embodiment shown in FIGS. 32 and 33, a bin or tray 1198 below the gravity chute portion 1190 receives and holds the relatively short dunnage products 1200 that fall through the gravity chute 1190.

The converter 1100 further includes a controller 1202 that enables selection of a desired length of dunnage products and controls the position of the output chute 1192. The controller 1202 typically includes a processor 1204, a memory 1206, and a program stored in the memory. The controller 1202 also includes one or more input devices 1210 for determining the selected length and one or more outputs for controlling elements of the conversion assembly 1154 and movement of the output chute 1192. The input devices 1210 can be connected to or include one or more of a keyboard, mouse, touch screen display, a scanner or sensor, a bar code reader for reading a bar code on a container that receives the dunnage products, a radio frequency identification device (RFID) sensor, microphone, camera, etc. The controller 1202 can be programmed to recognize the appropriate inputs that represent a selected length or identify a location to look up one or multiple lengths needed for a particular packing container.

Figure 37:
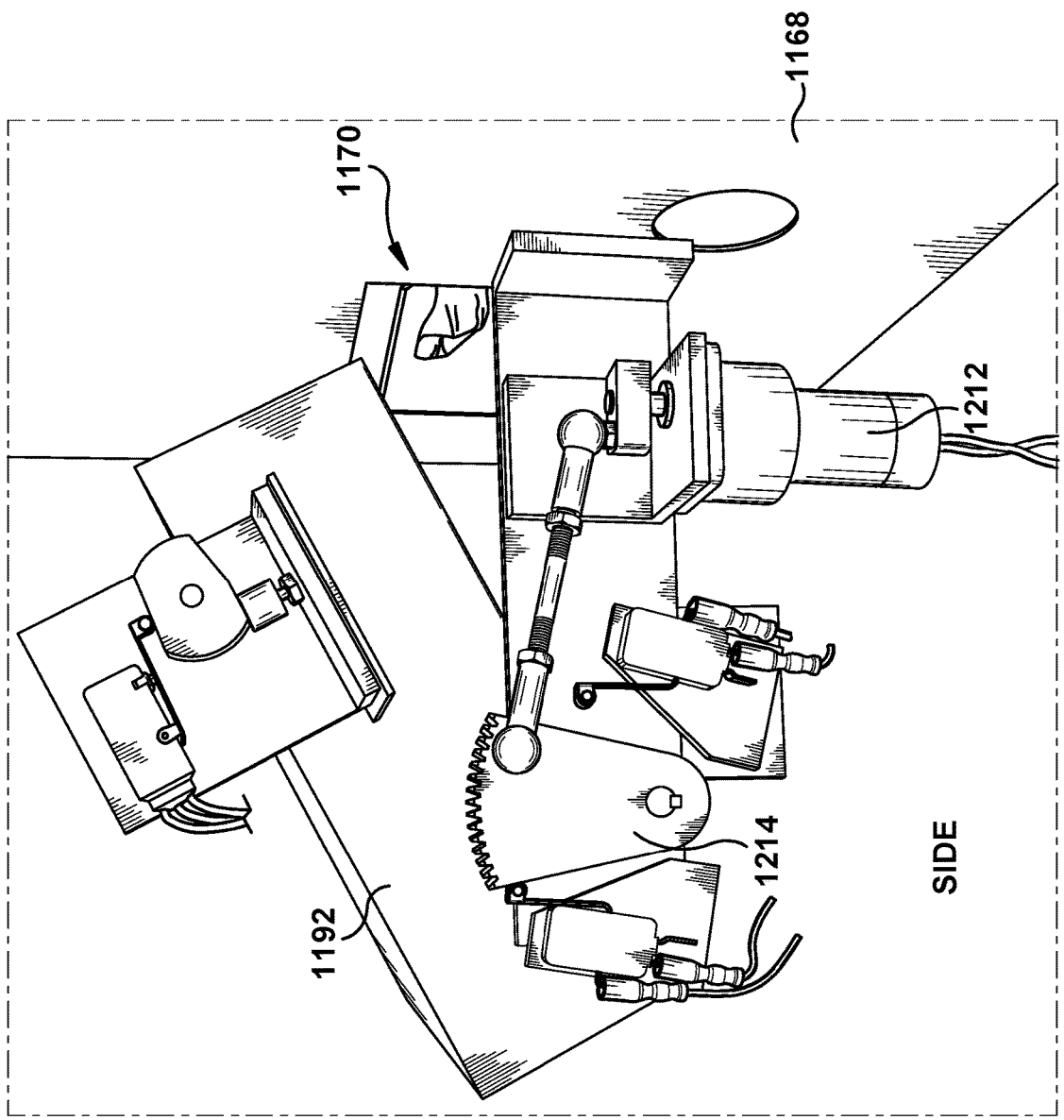
FIG. 37 is a side view of the output chute of FIG. 34 in a second position.
Figure 38:
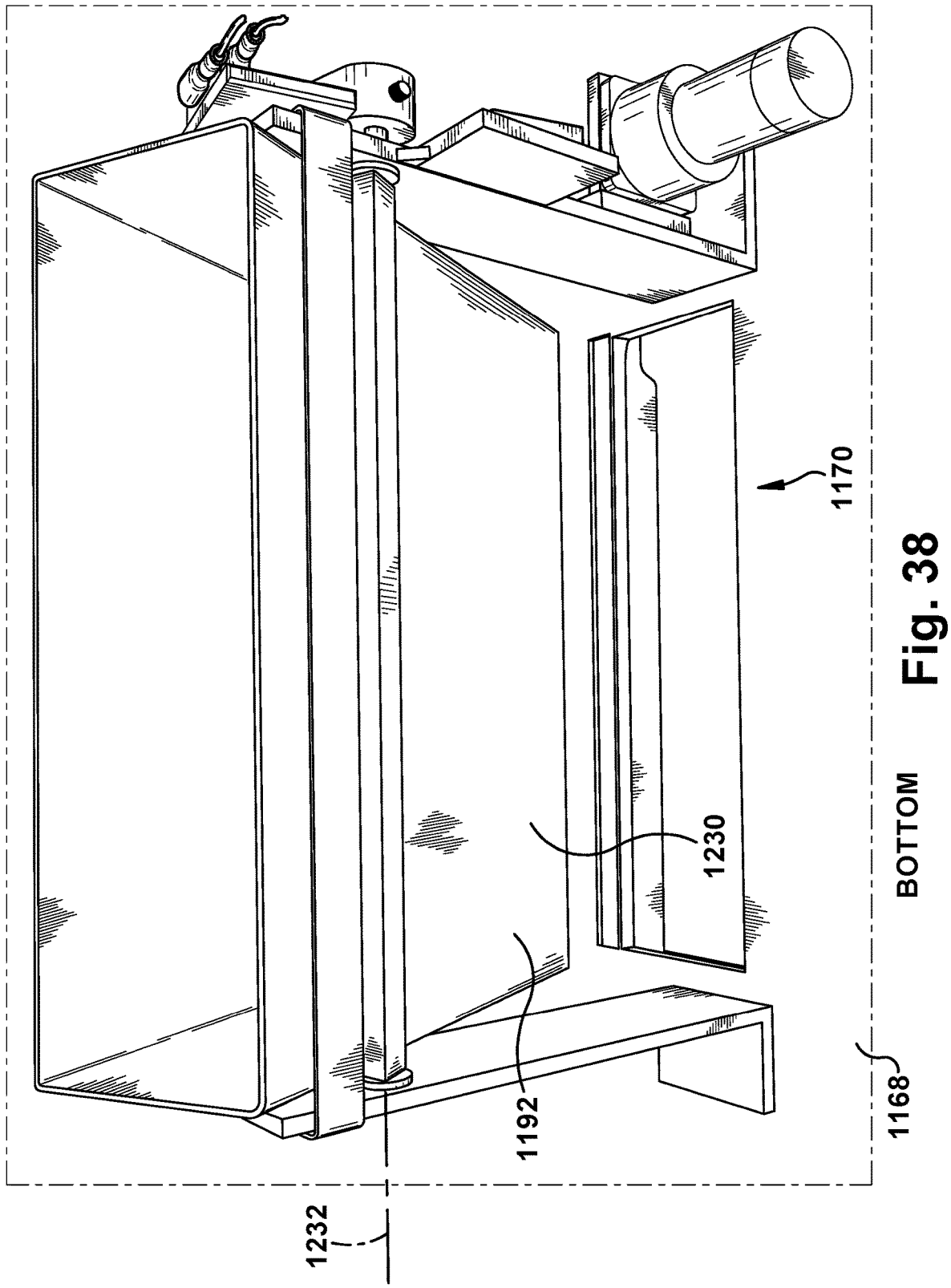
FIG. 38 is a bottom view of the output chute of FIG. 37.

The outputs from the controller 1202 can control various motors that drive elements of the conversion assembly 1154 and/or movement of the output chute 1192. In the embodiment shown in FIGS. 34-38, the controller 1202 controls a solenoid motor 1212 and a linkage 1214 to move the output chute 1192 from the first position (FIG. 34) to the second position (FIG. 37).

Converters often are located near a conveyor 1220 (FIG. 31) that transport packaging containers to be packed and shipped. Other work surface also are used for packing.

In the embodiment shown in FIGS. 34-38, the gravity chute portion 1190 has been omitted to improve the view of the outlet 1170 (FIGS. 37 and 38) and the output chute 1192. The output chute 1192 has walls 1220 that define a passage 1222 through the output chute. The output chute 1192 is movable between a first position where the output chute 1192 and the passage 1222 through the output chute 1192 are aligned with the outlet 1170 to receive relatively longer dunnage products 1124. In the first position, dunnage products 1224 having a length of at least a predetermined minimum length that are dispensed through the outlet 1170 enter the output chute 1192. And in the second position, the output chute 1192 is not aligned with the outlet 1170, so relatively short dunnage products 1200 having a length less than the predetermined minimum length that are dispensed through the outlet 1170 bypass the output chute 1192.

In the second position, a bottom surface 1230 of the output chute 1192 defines a guide surface to direct the dunnage products bypassing the output chute downward. The bottom of the output chute 1192 or guide surface 1230 is horizontally spaced downstream from the outlet 1170 and transverse a path of the dunnage products 1200 exiting the outlet 1170 in the downstream direction 1160. As the dunnage products 1200 exit the outlet 1170, if a leading edge extends far enough to engage the bottom 1230 of the output chute 1192, the inclined surface directs the dunnage products 1200 downward. As the dunnage products 120 clear the outlet 1170, they fall through the gravity chute 1190 (FIG. 32) for collection below the outlet 1170.

In the illustrated embodiment, the output chute 1192 is pivotable about an axis 1232 spaced from the outlet 1170 in the housing 1168, so that in the second position an upstream end of the output chute 1192 is rotatably spaced from the outlet 1170 and spaced from the position of the upstream end of the output chute 1192 in the first position. The pivot axis 1232 is substantially parallel to the plane of the outlet 1170, generally is horizontal, and generally is near the downstream end of the output chute 1192.

An exemplary method of dispensing dunnage products provided by the present invention includes the steps of: (a) converting a stock material into a dunnage product and dispensing the dunnage product through an outlet, (b) if the dunnage product has at least a predetermined minimum length, moving an upstream end of an output chute adjacent to and in alignment with the outlet to receive, support, and guide the dunnage product as it exits the outlet, and (c) if the dunnage product has a length that is less than the predetermined minimum length, moving the upstream end of the output chute relative to the outlet so that dunnage products exiting the outlet bypass the output chute.

In summary, the present invention provides a dunnage conversion machine that includes a shelf for supporting a supply of stock material, a conversion assembly for converting stock material into a dunnage product dispensed through an outlet, and a stand that supports the conversion assembly and the shelf. The shelf is linearly movable between an operating position adjacent the conversion assembly and a loading position spaced from the operating position for loading stock material without moving the conversion assembly. In the place of or in addition to the shelf, the conversion machine can include an output chute with an upstream end that is moveable relative to the outlet. In a first position, the output chute is aligned with the outlet to receive dunnage products, and in a second position the upstream end of the output chute is moved out of alignment with the outlet so that dunnage products from the conversion assembly bypass the output chute.

Although the invention has been shown and described with respect to a certain illustrated embodiment or embodiments, equivalent alterations and modifications will occur to others skilled in the art upon reading and understanding the specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function (i.e., that is functionally equivalent), even though not structurally equivalent to the disclosed structure which performs the function in the herein illustrated embodiment or embodiments of the invention.

What is claimed is:

1. A dunnage product comprising:
   a first sheet that is longitudinally crumpled with substantially parallel laterally-extending folds spaced at an irregular pitch;
   a second sheet that is connected face-to-face to the first sheet to hold the first sheet in its crumpled state;

wherein the resulting dunnage product has a width dimension parallel to the folds, a length dimension transverse the folds, and a thickness dimension transverse the width dimension and the length dimension, and the width dimension is greater than the thickness dimension, and the first sheet and the second sheet have substantially coextensive length and width dimensions;

wherein the first sheet is connected to the second sheet at regular intervals such that the length of the first sheet between connection points is irregular due to the irregular pitch of the folds in the first sheet.

2. A dunnage product as set forth in claim 1, wherein at least one of the first sheet and the second sheet includes paper.

3. A dunnage product as set forth in claim 1, wherein the first sheet and the second sheet are connected together along lines of mechanical interconnection.

4. A dunnage product as set forth in claim 3, wherein the first sheet and the second sheet are connected together along lines of mechanical interconnection adjacent lateral edges of the first sheet.

5. A dunnage product as set forth in claim 4, wherein the first sheet and the second sheet are connected together along a line of mechanical interconnection in a center of the first sheet.

6. A dunnage product as set forth in claim 3, wherein the lines of mechanical interconnection extend longitudinally along the length dimension.

7. A dunnage product as set forth in claim 1, wherein the first sheet and the second sheet are connected together along laterally-spaced longitudinally-extending lines of interconnection.

8. A dunnage product as set forth in claim 1, wherein the second sheet is uncrumpled.

9. A dunnage product as set forth in claim 1, wherein the first sheet is crumpled at a first average frequency, and the second sheet is crumpled at a second average frequency that is different from the first average frequency.

10. A dunnage product as set forth in claim 1, wherein the first sheet includes regularly-spaced lines of perforation along the length of the first sheet.

* * * * *